US011864797B2

(12) United States Patent
Samchukov et al.

(10) Patent No.: US 11,864,797 B2
(45) Date of Patent: Jan. 9, 2024

(54) ORTHOPEDIC SPRING HINGE SYSTEM AND METHODS THEREOF

(71) Applicant: Texas Scottish Rite Hospital for Children, Dallas, TX (US)

(72) Inventors: Mikhail L. Samchukov, Coppell, TX (US); John D. Ross, Ovilla, TX (US); Alexander M. Cherkashin, Flower Mound, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 60 days.

(21) Appl. No.: 17/185,344

(22) Filed: Feb. 25, 2021

(65) Prior Publication Data
US 2021/0177464 A1    Jun. 17, 2021

Related U.S. Application Data

(63) Continuation of application No. 15/994,829, filed on May 31, 2018, now Pat. No. 10,945,763.

(51) Int. Cl.
*A61B 17/60* (2006.01)
*A61B 17/64* (2006.01)
*A61B 17/62* (2006.01)

(52) U.S. Cl.
CPC .............. *A61B 17/60* (2013.01); *A61B 17/62* (2013.01); *A61B 17/6425* (2013.01); *A61B 2017/606* (2013.01)

(58) Field of Classification Search
CPC .............................................. A61B 2017/606
See application file for complete search history.

(56) References Cited

U.S. PATENT DOCUMENTS

| 3,727,610 A | * | 4/1973 | Riniker | A61B 17/6441 |
| | | | | 606/56 |
| 3,977,397 A | * | 8/1976 | Kalnberz | A61B 17/62 |
| | | | | 606/56 |
| 5,681,309 A | | 10/1997 | Ross, Jr. | |
| 6,030,386 A | | 2/2000 | Taylor | |
| 8,425,568 B2 | | 4/2013 | Bhatnagar | |
| 9,206,871 B2 | | 12/2015 | Phillips | |
| 10,413,328 B1 | | 9/2019 | Klein, Jr. | |
| 2005/0056979 A1 | | 3/2005 | Studer | |
| 2005/0127729 A1 | | 6/2005 | Knoblock et al. | |

(Continued)

OTHER PUBLICATIONS

International Search Report and Written Opinion received in corresponding Patent Cooperation Treaty Application No. PCT/US19/34700, dated Sep. 4, 2019, 13 pages.

(Continued)

*Primary Examiner* — Tessa M Matthews
(74) *Attorney, Agent, or Firm* — Haynes and Boone, LLP

(57) ABSTRACT

A device, kit, and method for the treatment of anatomical joint dysfunctions, and more particularly, to a spring hinge comprising: a primary coil spring having a helical structure with a central cavity, wherein the primary coil spring forms a plurality of spirals layered against one another when the primary coil spring is in an unexpanded state; wherein the primary coil spring comprises surfaces that are configured to nest against each other to resist translational or shearing movement between adjoining spiral layers.

22 Claims, 17 Drawing Sheets

(56) References Cited

U.S. PATENT DOCUMENTS

| | | | |
|---|---|---|---|
| 2006/0229612 A1* | 10/2006 | Rothman | A61B 17/7028 606/279 |
| 2007/0049930 A1 | 3/2007 | Hearn et al. | |
| 2008/0191400 A1* | 8/2008 | Liu | F16F 1/042 267/195 |
| 2010/0228298 A1* | 9/2010 | Bhatnagar | A61B 17/7032 606/279 |
| 2010/0320660 A1 | 12/2010 | Takeda et al. | |
| 2011/0208187 A1 | 8/2011 | Wong | |
| 2014/0131932 A1* | 5/2014 | Balsells | B21F 35/02 267/167 |
| 2014/0292973 A1* | 10/2014 | Terada | B41J 13/009 347/104 |
| 2018/0250139 A1 | 9/2018 | Luboshitz | |
| 2019/0110816 A1 | 4/2019 | Ross | |

OTHER PUBLICATIONS

Chaudhury, A et al. "Analysis of prismatic springs of non-circular coil shape and non-prismatic 21 springs of circular coil shape by analytical and finite element methods." Journal of Computational Design and Manufacturing. Feb. 8, 2017; pp. 178-191.

* cited by examiner

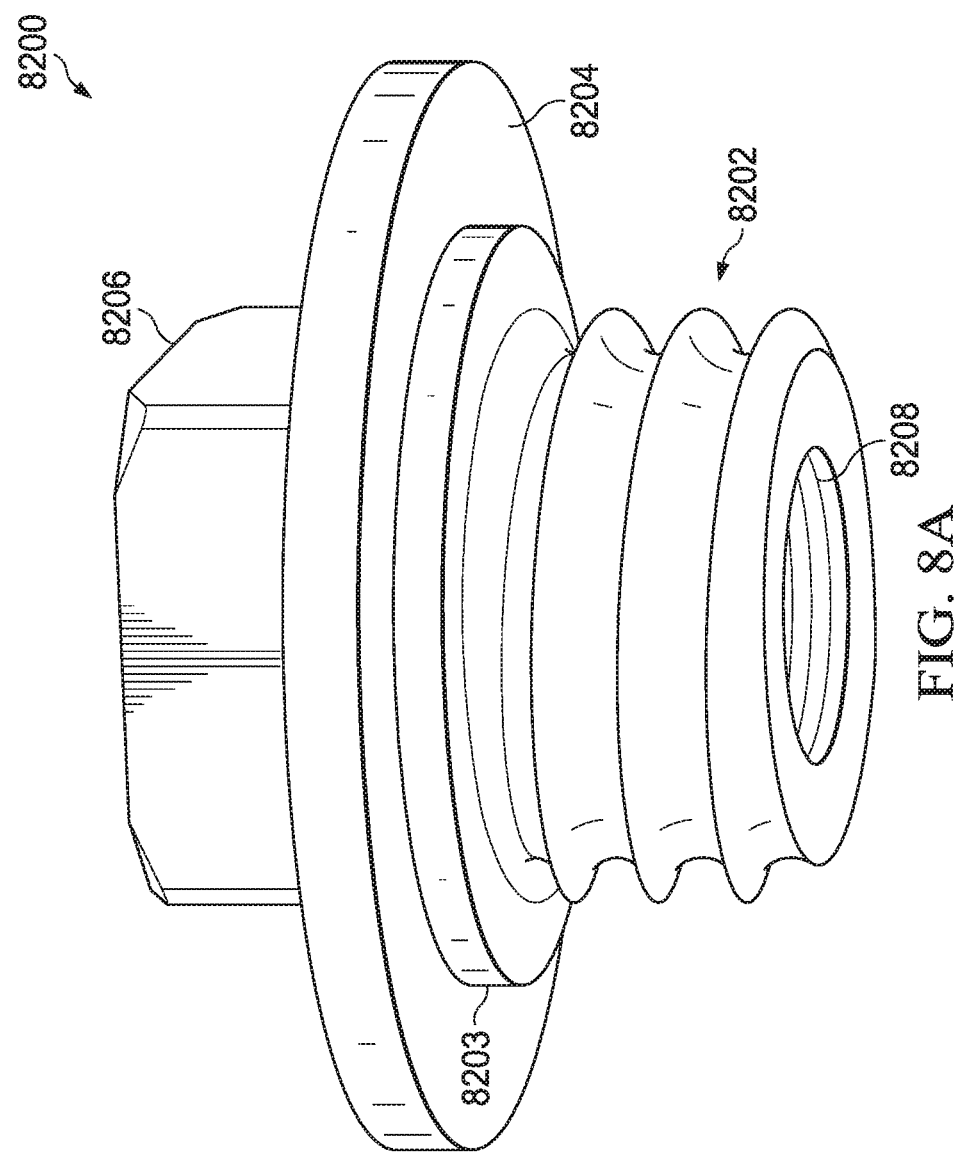

ORTHOPEDIC SPRING HINGE SYSTEM AND METHODS THEREOF

CROSS REFERENCE TO RELATED APPLICATIONS

This application is a continuation of pending U.S. patent application Ser. No. 15/994,829 filed May 31, 2018 and entitled "Orthopedic Spring Hinge System and Methods Thereof," which is hereby incorporated by reference in its entirety for all purposes.

FIELD OF THE DISCLOSURE

The present disclosure relates, in some embodiments, to orthopedic hinge devices and systems suitable for use as part of external fixation systems.

BACKGROUND OF THE DISCLOSURE

Without limiting the scope of the disclosure, this background is described in connection with orthopedic hinges for use with external fixators and external fixation systems. Generally, external fixators are commonly used in a variety of surgical procedures including limb lengthening, deformity correction, fracture reduction, and treatment of non-unions, mal-unions, and bone defects. The process involves a rigid framework comprising several external fixators, such as external fixation rings, that are placed externally around the limb and attached to bone segments using wires and half pins, which are inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other at the time of application or after manipulation of bone segments either rapidly (acutely) or gradually over a period of time.

For treatment of various pathologies, it is beneficial to allow for controlled movement about a hinge that is disposed between two external fixator supports. Introducing controlled movement can accelerate bone healing and improve mobility of joints. For example, it may be beneficial to secure one or more hinges between two external supports to allow for limited pivotal movement of an anatomical joint. A hinge may allow for pivotal rotation of an anatomical joint such that movement may be reintroduced to a patient's joint. Such hinges, however, should provide for sufficient stability and prevent unwanted movement along axes other than the anatomical joint. Unwanted movement along axes other than the anatomical joint may negatively impact the healing process and otherwise cause damage to a patient's anatomical joint. For example, translational movement or shearing of the hinge during pivotal movement may harm the anatomical joint and impair healing or movement of the anatomical joint. Translational or shearing movement may occur along a plane orthogonal to the lengthwise axis of the hinge.

Traditional mono-axial mechanical hinges have been used in orthopedic treatment but have significant limitations. Mechanical pin hinges may not adequately conform to the anatomical axis of a patient's anatomical joint, particularly if the joint axis changes dynamically. When an anatomical joint rotates or moves, the corresponding anatomical axis of rotation may shift in three dimensions. Furthermore, many anatomical joints are highly complex, such as the ankle and wrist, and do not simply follow a static axis of rotation. Using a mechanical pin hinge to introduce motion to an anatomical joint may therefore be limited since a mechanical pin hinge is static and would not be dynamically adjust to the dynamic anatomical axes of rotation. If a mechanical pin hinge is used in conjunction with external fixators, the patient's joint may not be able to adequately or comfortably pivot. Further, if the mechanical pin hinge's axis of rotation is out of alignment with the anatomical axis of rotation, pivoting about the anatomical joint could result in pain, discomfort, subluxation or dislocation of the joint, and/or damage to the anatomical joint.

Springs may serve as hinges that may allow for the axis of rotation to shift or adjust to the position of the anatomical axis of rotation of a particular anatomical joint during rotation or movement of said anatomical joint. However, springs have relatively higher instability and would not limit the degrees of movement to a particular plane or along one direction. When a spring is bending in a particular direction, the internal layers that make up the spring are readily susceptible to shearing forces and movement, resulting in the spring also exhibiting a translational or shearing movement. Accordingly, traditional springs fail to provide sufficient stability and would also be likely to result in pain, discomfort, and/or damage to the anatomical joint if used with external fixators.

Accordingly, there is a need for improved hinges that provide for sufficient stability, can limit the pivotal movement to a finite number of planes or directions, while also being able to dynamically adapt to the shifting anatomical axis of rotation during movement of a corresponding anatomical joint.

SUMMARY

The present disclosure relates in general to orthopedic hinges suitable for use with external fixators and as part of external fixation systems. In some embodiments, orthopedic hinges of the present disclosure may provide for pivotal movement about an anatomical joint while substantially or completely preventing unwanted translational or shearing movement or sheering about said anatomical joint.

In some embodiments, a spring hinge comprises a primary coil spring having a helical structure with a central cavity, wherein the primary coil spring forms a plurality of spirals layered against one another when the primary coil spring is in an unexpanded state, wherein the primary coil spring comprises a first surface having a convex profile in a first direction and a second surface having a concave profile in a second direction opposite to the first direction, wherein a portion of the first surface with the convex profile is configured to nest against an adjacent portion of the second surface with the concave profile when the primary coil spring is in an unexpanded state, and wherein the nested convex and concave profiles resist a shearing movement between the first surface and the second surface.

In some embodiments, the spring hinge may comprise a primary coil spring with spring constant of about 10-20 lb/in.

In some embodiments, a cross section of the primary coil spring along a transverse plane comprises a geometry selected from the group consisting of a rectangle, pentagon, and hexagon.

In some embodiments, a cross section along a transverse plane of the primary coil spring comprises a square geometry.

In some embodiments, the primary coil spring has a width of about 5 to 25 mm.

In some embodiments, the primary coil spring has a length of about 15 to 50 mm.

In some embodiments, the spring hinge further comprises an end cap at each of the primary coil spring, wherein the end caps are configured to be secured to a ring fixator.

In some embodiments, the spring hinge is secured to a ring fixator.

In some embodiments, the primary coil spring is positioned to bend along an anatomical axis.

In some embodiments, the primary coil spring is constructed from materials selected from the group consisting of stainless steel, plated spring-tempered steel, and coated spring-tempered steel.

In some embodiments, the spring hinge further comprises a secondary coil spring disposed within the central cavity of the primary coil spring.

In some embodiments, the secondary coil spring deters shearing between the first surface with the convex profile and the second surface with the concave profile, and the secondary coil spring stabilizes movement of the primary coil spring when moving from the unexpanded state to an expanded state.

In some embodiments, the secondary coil spring has a spring constant of about 10-20 lb/in.

In some embodiments, a cross section along a transverse plane of the secondary coil spring comprises a circular geometry with diameter of about 5 to 25 mm.

In some embodiments, the secondary coil spring has a length substantially similar to a length of the primary coil spring.

In some embodiments, the secondary coil spring is constructed from materials selected from the group consisting of stainless steel, plated spring-tempered steel, and coated spring-tempered steel.

In some embodiments, a spring hinge comprises a primary coil spring having a helical structure with a central cavity, wherein the primary coil spring forms a plurality of spirals layered against one another when the primary coil spring is in an unexpanded state; and a secondary coil spring disposed within the central cavity of the primary coil spring, wherein the primary coil spring resists shearing movement of the spirals of the primary coil spring.

In some embodiments, the primary coil spring comprises a first surface having a convex profile in a first direction and a second surface having a concave profile in a second direction opposite to the first direction, wherein a portion of the first surface is configured to nest against an adjacent portion of the second surface when the primary coil spring is in an unexpanded state, and wherein the convex profiles and convex profiles resist shearing movement between the first surface and the second surface.

In some embodiments, the primary coil spring comprises a first planar surface having a slanted profile facing a first direction and a second planar surface having a slanted profile facing a second direction, wherein a portion of the first planar surface is configured to abut a portion of the second planar surface of an adjacent spiral when the primary coil is in an unexpanded state, and wherein the slanted profiles of the first planar surface and the second planar surface resist shearing movement between the first planar surface and the second planar surface.

In some embodiments, the primary coil spring has a spring constant of about 0.5-5.0 lb/in, and the secondary coil spring has a spring constant of about 10-20 lb/in.

In some embodiments, a cross section along a transverse plane of the primary coil spring comprises a geometry selected from the group consisting of a rectangle, pentagon, and hexagon.

In some embodiments, the primary coil spring and the second coil spring each have a length of about 15 to 50 mm.

In some embodiments, the spring hinge further comprises an end cap at each of the primary coil spring, wherein the end caps are configured to be secured to a ring fixator.

In some embodiments, the spring hinge is secured to a ring fixator.

In some embodiments, a spring hinge comprises a primary coil spring having a helical structure with a central cavity, wherein the primary coil spring comprises a plurality of spirals layered against one another when the primary coil spring is in an unexpanded state, a first end cap comprising a threaded portion for coupling to a first end of the primary coil spring, a securing feature for mounting the first end cap to an external fixation system, and a second end cap comprising a threaded portion for coupling to a second end of the primary coil spring, a securing feature for mounting the second end cap to an external fixation system, wherein the primary coil spring comprises a first planar surface having a slanted profile facing a first direction and a second planar surface having a slanted profile facing a second direction, wherein a portion of the first planar surface is configured to abut a portion of the second planar surface when the primary coil is in an unexpanded state, and wherein the slanted profiles of the first planar surface and the second planar surface deter sheering between the first planar surface and the second planar surface, and stabilizes movement of the primary coil spring when moving from the unexpanded state to an expanded state.

In some embodiments, the primary coil spring has a spring constant of about 0.5-5.0 lb/in.

In some embodiments, the spring hinge further comprises a secondary coil spring disposed within the central cavity of the primary coil spring.

In some embodiments, a cross section of the primary coil spring along a transverse plane comprises a geometry selected from the group consisting of a rectangle, pentagon, and a hexagon.

In some embodiments, the primary coil spring and the second coil spring each have a length of about 15 to 50 mm.

In some embodiments, a spring hinge comprises a primary coil spring having a helical structure with a central cavity, wherein the primary coil spring comprises a plurality of spirals, and an interstitial coil spring having a helical structure with a central cavity, wherein the interstitial coil spring comprises a plurality of spirals, wherein the plurality of spirals of the interstitial coil spring and disposed in between the plurality of spirals of the primarily coil spring, and wherein the interstitial coil spring deters sheering between the primary coil and the interstitial coil, and stabilizes movement of the primary coil spring when moving from the unexpanded state to an expanded state.

In some embodiments, a method for treating an anatomical joint dysfunction may comprise fixing a first and a second portion of a limb on opposite sides of an anatomical joint with a first and a second external fixator, such that the first and second external fixators are positioned on either side of the anatomical joint, connecting the first and second external fixators with an orthopedic spring hinge, wherein the orthopedic spring hinge comprises a primary coil spring having a helical structure with a central cavity, wherein the primary coil spring forms a plurality of spirals layered against one another when the primary coil spring is in an unexpanded state, wherein the primary coil spring comprises a first surface having a convex profile in a first direction and a second surface having a concave profile in a second direction opposite to the first direction, wherein a portion of the first surface with the convex profile is configured to nest against an adjacent portion of the second surface with the concave profile when the primary coil spring is in an unexpanded state, and wherein the nested convex and concave profiles resist shearing movement between the first surface and the second surface, and wherein the orthopedic spring hinge provides for a pivotal movement about the anatomical joint while substantially or completely preventing unwanted translational or shearing movement, or sheering, about said anatomical joint.

In some embodiments, the spring hinge further comprises a secondary coil spring disposed within the central cavity of the primary coil spring.

In some embodiments, a kit may comprise one or more spring hinges, each spring hinge comprising a primary coil spring having a helical structure with a central cavity, wherein the primary coil spring forms a plurality of spirals layered against one another when the primary coil spring is in an unexpanded state, wherein the primary coil spring comprises a first surface having a convex profile in a first direction and a second surface having a concave profile in a second direction opposite to the first direction, wherein a portion of the first surface with the convex profile is configured to nest against an adjacent portion of the second surface with the concave profile when the primary coil spring is in an unexpanded state, and wherein the nested convex and concave profiles resist a shearing movement between the first surface and the second surface, and one or more optional external fixators, screws, bolts, or end caps.

BRIEF DESCRIPTION OF THE DRAWINGS

Some embodiments of the disclosure may be understood by referring, in part, to the present disclosure and the accompanying drawings, wherein:

FIG. 8A illustrates a portion of an external fixation system according to a specific example embodiment of the disclosure;

DETAILED DESCRIPTION

Figure 1:
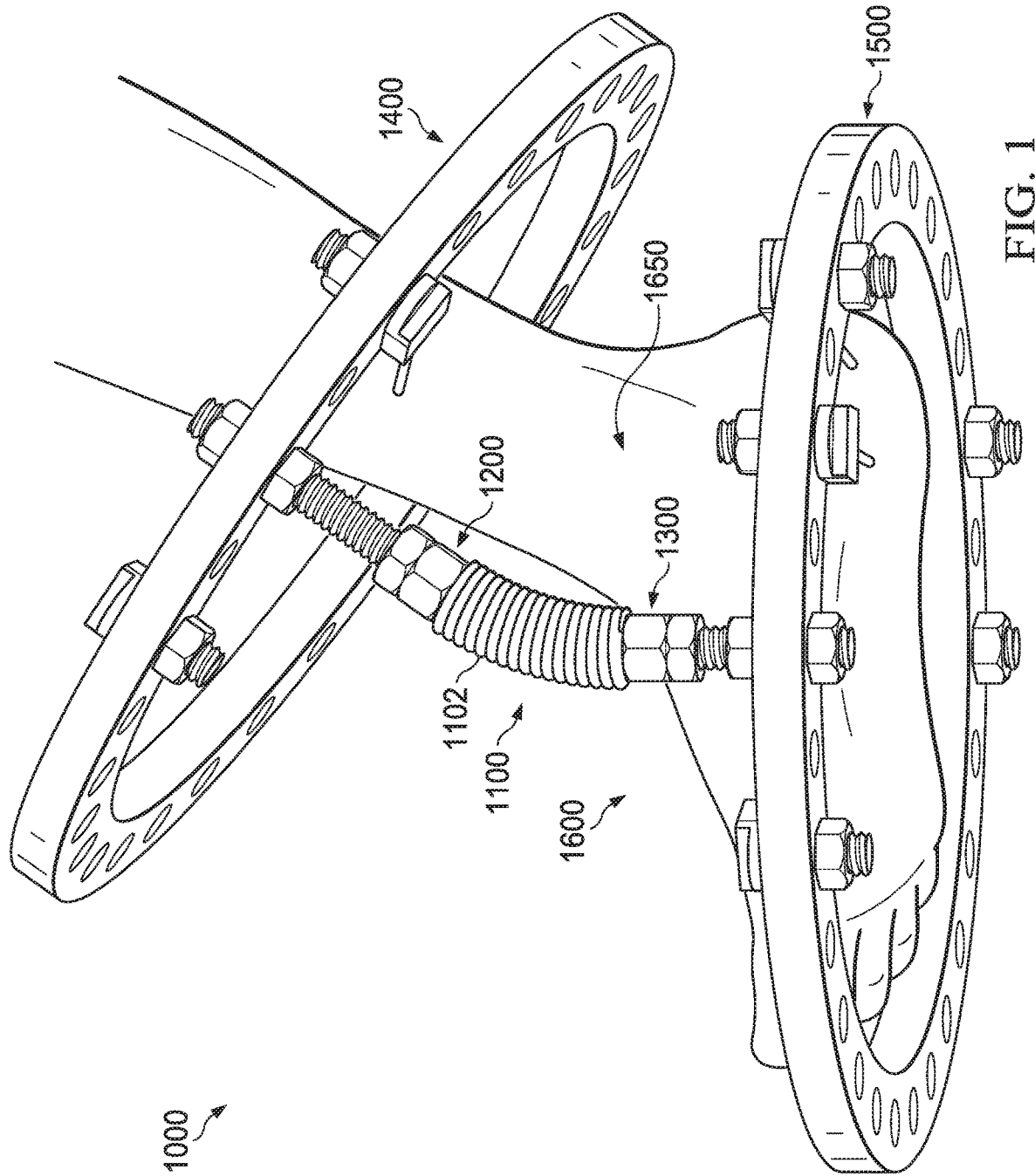
FIG. 1 illustrates an external fixation system according to a specific example embodiment of the disclosure.

The present disclosure relates, in some embodiments, to orthopedic hinges suitable for use with external fixation devices. Orthopedic hinges of the present disclosure may be suitable for treatment of various anatomical joints including, but not limited to, the wrist, elbow, knee, or ankle.

According to some embodiments, an orthopedic hinge may comprise a spring hinge suitable for use with an external fixator such as an external fixation ring. The spring hinge may comprise a primary coil spring having a helical structure. The primary coil may form a plurality of spirals that are layered or stacked upon one another. When the spring hinge is in an unexpanded state, the layers of spirals may rest upon one another. In some embodiments, a coil of a spring hinge may comprise materials such as 302 stainless steel, spring-tempered steel, music wire spring, plated and/or polymer-coated with a plastic, polymer, and/or other resilient materials.

Non-limiting examples of polymers for use as the coils and/or a coating for the coils include, but are not limited to, polytetrafluoroethylene (PTFE), ethylene tetrafluoroethylene (ETFE), fluorinated ethylene propylene (FEP), polyoxymethylene (POM), polyether block ester, polyurethane (for example, Polyurethane 85A), polypropylene (PP), polyvinylchloride (PVC), polyether-ester, ether or ester based copolymers (for example, butylene/poly(alkylene ether) phthalate and/or other polyester elastomers), polyamide, elastomeric polyamides, block polyamide/ethers, polyether block amide (PEBA), ethylene vinyl acetate copolymers (EVA), silicones, polyethylene (PE), Marlex high-density polyethylene, Marlex low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonates, ionomers, biocompatible polymers, other suitable materials, or mixtures, combinations, copolymers thereof, polymer/metal composites, and the like.

Non-limiting examples of metals and metal alloys for use with the present invention include, e.g., stainless steel, such as 304V, 304L, and 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, nickel-chromium alloys, nickel-molybdenum alloys, nickel-cobalt alloys, nickel-iron alloys, nickel-copper alloys, nickel-tungsten or tungsten alloys, and the like; cobalt-chromium alloys; cobalt-chromium-molybdenum alloys; platinum enriched stainless steel; titanium; combinations thereof; and the like; or any other suitable materials with sufficient mechanical strength to control movement of a joint (prevent shear and/or displacement) during an orthopedic treatment.

Spring hinges of the present disclosure may comprise certain features that advantageously allow for pivotal movement about an anatomical joint while substantially or completely preventing unwanted translational or shearing movement about said anatomical joint. Further, embodiments of the present disclosure may limit the pivotal movement of an anatomical joint to a finite number of planes or directions, while also being able to dynamically adapt to the shifting anatomical axis of rotation during movement of a corresponding anatomical joint.

FIG. 1 depicts an example embodiment of the present disclosure. As depicted, the present disclosure provides for an external fixation system 1000 comprising a spring hinge 1100 that may be used in conjunction with a plurality of external fixators, such as external fixation rings 1400, 1500. In some embodiments, external fixation rings 1400, 1500 may be separated by only a few centimeters. Preferably this separation is sufficient to allow one ring 1500 to pivot through the full range of motion associated with the anatomical joint 1650.

Spring hinge 1100 may comprise a coil spring. The coil spring may comprise a plurality of spirals 1102 that are stacked or layered on top of one another. Each spiral 1102 or layer of the coil spring may merge curvilinearly with an adjacent spiral or layer. For example, a spiral 1102 may merge curvilinearly with a spiral positioned above it and a spiral positioned below it. The coil spring of the spring hinge 1100 may be connected at both ends to an end cap 1200, 1300. The end caps 1200, 1300 may be secured, either directly or indirectly, to the external fixation rings 1400, 1500 of the external fixation system 1000.

In some embodiments, an external fixation system 1000 of the present disclosure may be secured around an anatomical region 1600. An anatomical region 1600 may be selected based on a region in need of treatment, such as a region with a fracture, an anatomical joint, or a region that has undergone a surgical procedure. As depicted, the anatomical region 1600 may coincide with an anatomical joint 1650, such as an ankle. However, embodiments of the present disclosure may also be used for joints such as a wrist, elbow, or knee. In use, spring hinge 1100 may allow for controlled movement of the anatomical joint 1650. Spring hinge 1100 may pivot or bend in a manner such that the axis (or axes) of rotation aligns with the axis (or axes) of the anatomical joint 1650. Further, the axis of rotation of the spring hinge 1100 may shift dynamically to align with shifting of the anatomical axis of rotation of the anatomical joint 1650 as the anatomical joint 1650 bends. When an anatomical joint 1650, such as an ankle, bends, the axis of rotation of the joint does not remain static but shifts its position and/or orientation during movement or rotation of the ankle. Present embodiments may advantageously provide for spring hinges 1100 where the axis of rotation of the spring hinges 1100 may dynamically shift so as to align with the anatomical axis of rotation of the anatomical joint 1650. As a result, when used in conjunction with external fixators for orthopedic treatment, present embodiments significantly reduce the potential for harm or injury that may result in using a hinge with a static axis of rotation, such as traditional mechanical pin hinges.

In some embodiments, the axis of rotation may be orthogonal to the lengthwise axis of the hinge. Described here, the lengthwise axis may be the axis that runs along the length of the spring hinge 1100 when the spring hinge 1100 is in a resting, unstressed state. In some embodiments, the spring hinge 1100 may be linear or curved in a resting, unstressed state. Thus, the lengthwise axis may also be linear or curved depending on the geometry of the spring hinge 1100.

Figure 2:
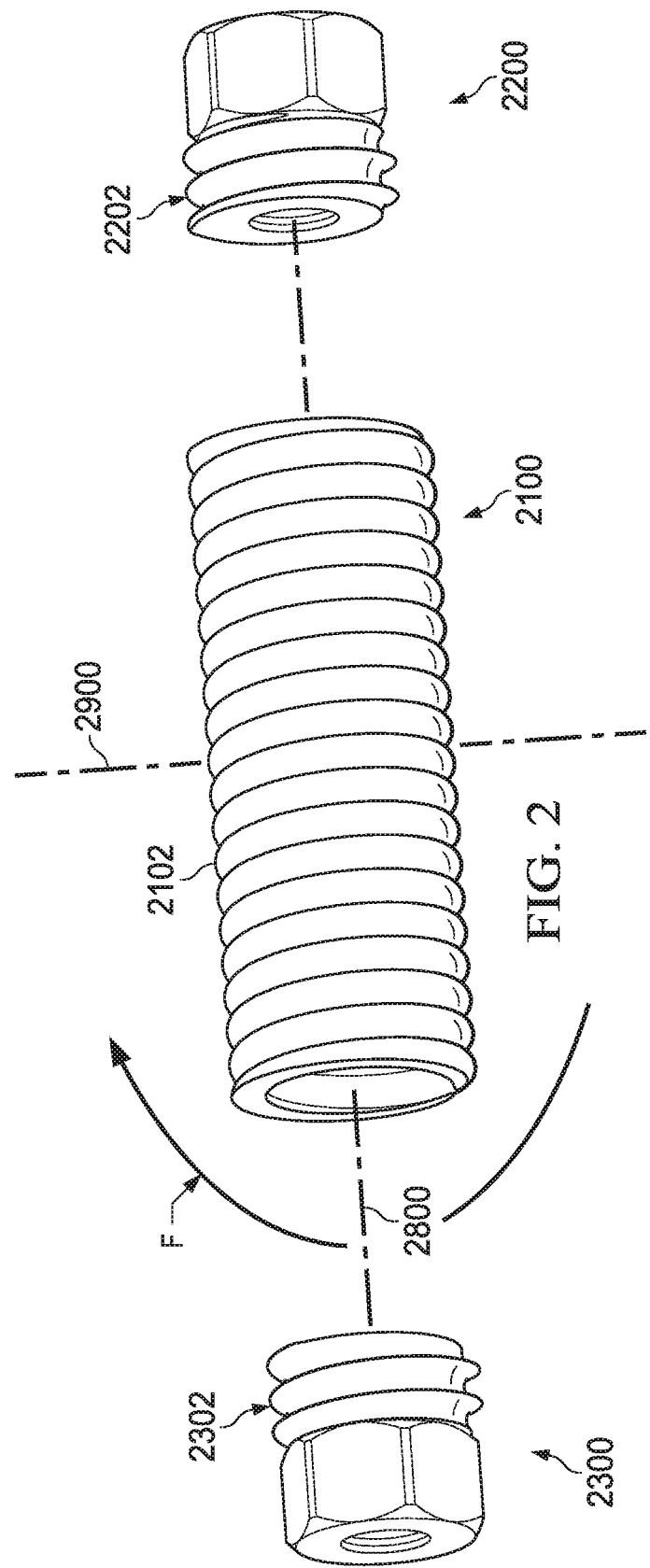
FIG. 2 illustrates a spring hinge according to a specific example embodiment of the disclosure.

FIG. 2 depicts an example spring hinge 2100 of the present disclosure. As depicted, spring hinge 2100 may be a coil spring comprising a plurality of spirals 2102. In some embodiments, the plurality of spirals of the spring hinge 2100 may be disposed adjacent to one another. The spring hinge 2100 may be configured to be secured to end caps 2200, 2300. End caps 2200, 2300 may each comprise a plurality of threads 2202, 2302. The plurality of threads 2202, 2302 may be configured to be threaded against the plurality of spirals 2102 at either end of the spiral hinge 2100. In a preferred embodiment, the threads 2202, 2302 of the end caps 2200, 2300 mate with the interior surface of the coil spring. End caps 2200, 2300 may advantageously facilitate securing the spiral hinge 2100 to an external fixation system.

The spring hinge 2100 may be substantially aligned along a lengthwise axis 2800. End caps 2200, 2300 may also be substantially aligned along this lengthwise axis. A rotation axis 2900 may be defined orthogonal to the lengthwise axis 2800. The rotation axis 2900 may correspond to the axis of rotation of spring hinge 2100. For example, the spring hinge 2100 may pivot or bend about the rotation axis 2900 when a force (F) perpendicular to the lengthwise axis 2800 is applied to the spring hinge 2100.

Regardless of whether the lengthwise axis 2800 is linear (e.g. the spring hinge may have a curved resting state), the rotation axes 2900 may or may not be orthogonal to the lengthwise axis 2800. It is understood that a rotation about an axis not orthogonal to the lengthwise axis can be decomposed, without loss of generality, into a rotation about an axis orthogonal to the lengthwise axis (a "swing"), followed by a rotation about an axis parallel to the rotation axis (a "twist"). Therefore, pivots or rotations about an axis not orthogonal to the lengthwise axis comprise a (generally non-zero) twist component.

Further, "compound" pivots of the spring hinge about multiple axes of rotations may be possible, e.g. in the case of applying a pivot to a spring hinge that is curved in its unstressed, resting state (as the curved resting state would at least comprise a first "swing" rotation relative to a linear spring hinge). However, it is also noted that compound pivots may degenerate (i.e. correspond) to a pivot about one axis of rotation. For example, in the case of a spring hinge that is curved in its unstressed, resting state, a second "swing" pivot, about an axis of rotation that lies on a plane which intersects the point of rotation of the original spring curve and is orthogonal to the lengthwise axis of the spring hinge at that point, would result in the spring hinge assuming a final state equivalent to a single "swing" pivot being applied to a spring hinge with a linear lengthwise axis.

In some embodiments, the spring hinge 2100 may have a length of about 5-50 mm, e.g. 27 mm. The spring hinge 2100 may also have a diameter or a width of about 2-30 mm, e.g. 13 mm Each spiral or layer of the coil spring may have a thickness of about 0.5-5 mm, e.g. 1.6 mm. In some embodiments, the spring hinge 2100 may have a spring constant of about 10-20 lb/in, but can have a spring constant of 5 to 50 lb/in.

Figure 3:
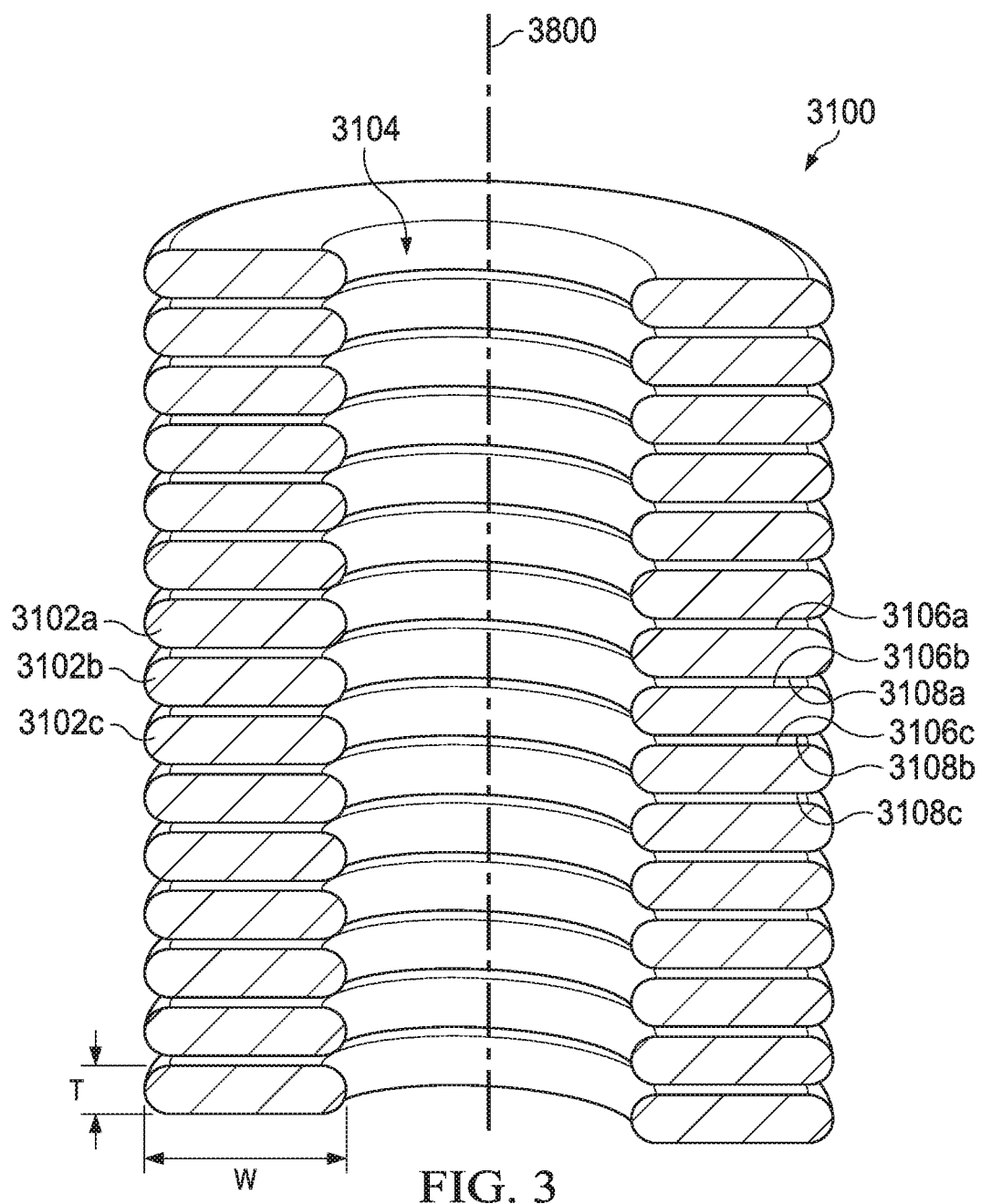
FIG. 3 illustrates a cross section of a spring hinge according to a specific example embodiment of the disclosure.

FIG. 3 depicts a cross section of a spring hinge 3100 according to some embodiments of the present disclosure. Spring hinge 3100 may comprise a coil spring having a helical structure such that the helical structure forms a plurality of spirals 3102a, 3102b, 3102c. The coil structure of the spring hinge 3100 may comprise a central cavity 3104 that runs through a length of the spring hinge 3100. In some embodiments, the central cavity 3104 may have a diameter of about 2-25 mm, e g 9.5 mm. The plurality of spirals 3102a, 3102b, 3102c may encircle or surround the central cavity 3104. Each of the plurality of spirals 3102a, 3102b, 3102c may merge curvilinearly into a spiral above and/or below it so as to form a continuous coil.

In some embodiments, when the coil is in an unexpanded or resting state, the plurality of spirals 3102a, 3102b, 3102c may be in contact or may touch an adjacent spiral. For example, a spiral 3102a may comprise an upper surface 3106a and a lower surface 3108a. As used herein, upper and lower are used in reference to a particular position of the spring hinge 3100. One of ordinary skill in the art having the benefit of the present disclosure would understand that the terms upper and lower are relative and that adjusting the position and/or orientation of the spring hinge 3100 would alter the usage of said terms.

The lower surface 3108a of a spiral 3102a may be in contact with or rest against an upper surface 3106b of an adjacent spiral 3102b. Further, a lower surface 3108b of spiral 3102b may also be in contact with or rest against an upper surface 3106c of an adjacent spiral 3102c. Similarly, upper surface 3106a may be in contact with an adjacent spiral above spiral 3102a. Lower surface 3108c may be in contact with or may abut an adjacent spiral below spiral 3102c.

As depicted in FIG. 3, the upper surfaces 3106a, 3106b, 3106c and the lower surfaces 3018a, 3018b, 3018c of the plurality of spirals 3102a, 3102b, 3102c may have a flat or planar cross-sectional profile. In a cross section of the plurality of spirals 3102a, 3102b, 3102c, the upper surfaces 3106a, 3106b, 3106c may be flat or planar and the lower surfaces 3108a, 3108b, 3108c may be flat or planar. In some embodiments, the flat or planar surfaces of the upper surfaces 3106a, 3106b, 3106c and the lower surfaces 3108a, 3108b, 3108c may be substantially orthogonal to a lengthwise axis 3800 of the spring hinge 3100. The lengthwise axis 3800 of the spring hinge may be defined by the direction in which the central cavity 3014 runs when the spring hinge 3100 is in a resting state. The relatively high width W to thickness T ratio of the spirals helps to resist translational or shearing movement of the adjacent spirals of the spring hinge 3100.

The flat or planar surfaces of the upper surfaces 3106a, 3106b, 3106c and the lower surfaces 3108a, 3108b, 3108c may advantageously provide for a frictional contact between adjacent surfaces, such as between lower surface 3108a and upper surface 3016b or between lower surface 3108b and upper surface 3106c. The frictional contact may deter translational or shearing movement of the upper surfaces 3106a, 3106b, 3106c with respect to the lower surfaces 3108a, 3108b, 3108c. In use, the spring hinge 3100 may bend or curve about its lengthwise axis 3800 with little to no translational or shearing movement of the upper surfaces 3106a, 3106b, 3106c with respect to the lower surfaces 3108a, 3108b, 3108c.

In some embodiments, the upper surfaces 3106a, 3106b, 3106c and the lower surfaces 3108a, 3108b, 3108c may have a width of about 0.5-10 mm, e.g. 3.2 mm A longer width of the upper surfaces 3106a, 3106b, 3106c and the lower surfaces 3108a, 3108b, 3108c may advantageously provide for greater contact surface and friction between adjacent surfaces and may thereby deter or resist translational or shearing movement of the spirals within the coil spring. Additionally, the spring hinge 3100 material and/or surface treatment may further deter translational or shearing movement of the spring coils with respect to one another. Such spring hinge 3100 materials may include 302 stainless steel, spring-tempered steel bead blasted in glue, and/or other resilient materials, and surface treatments may include a textured surface, plain or plated or coated with a material such as polyurethane to enhance friction between coil layers, and/or roughening treatments that create imperfections in the material surface.

Figure 4A:
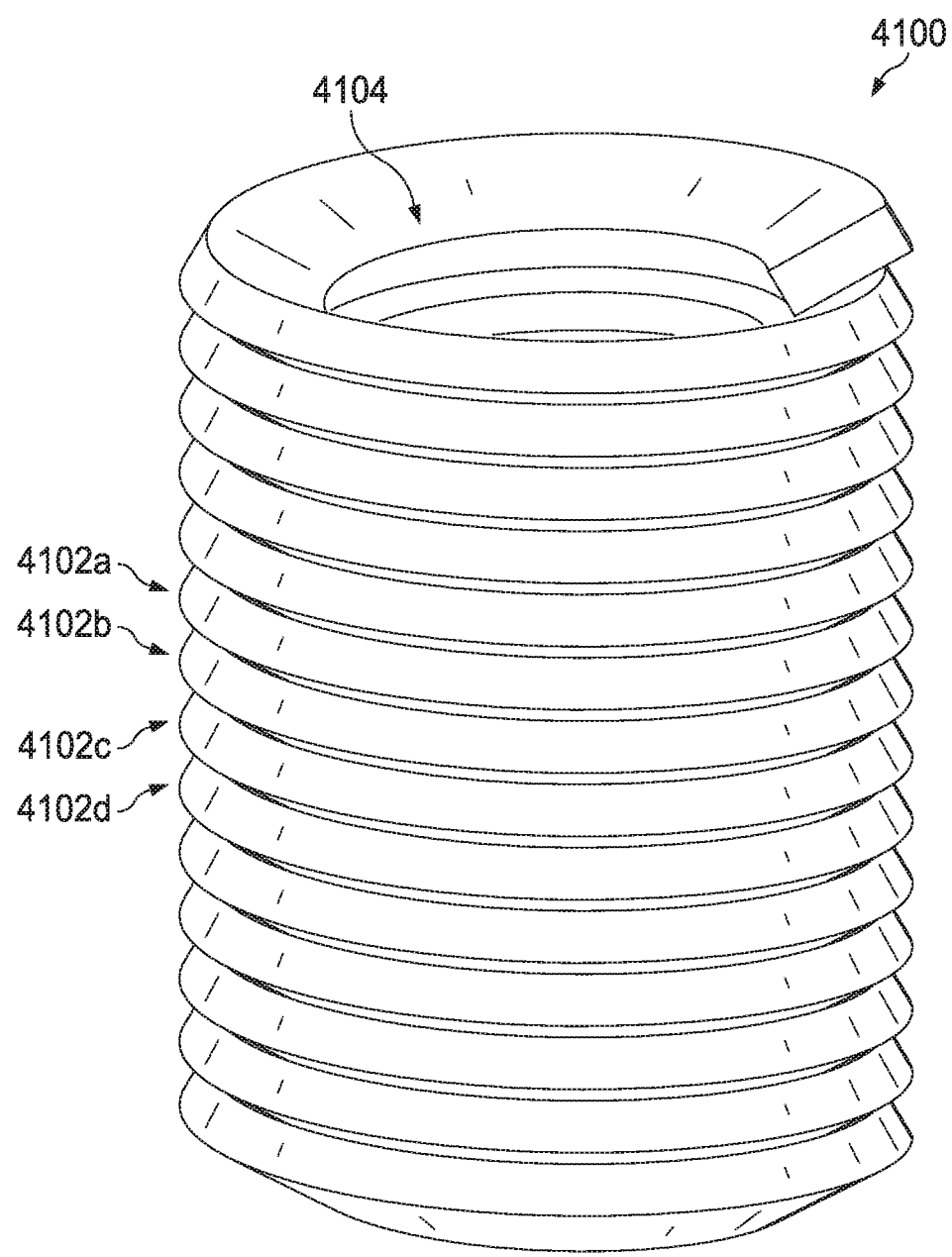
FIG. 4A illustrates a spring hinge according to a specific example embodiment of the disclosure.

FIG. 4A depicts a spring hinge 4100 according in some embodiments of the present disclosure. As depicted, spring hinge 4100 may comprise a plurality of spirals 4102a, 4102b, 4102c, 4102d, and a central cavity 4104. Each of the plurality of spirals 4102a, 4102b, 4102c, 4102d may be in physical contact with adjacent spirals, both above and below, when the spring hinge 4100 is not stretched or is in an unexpanded resting state.

Figure 4B:
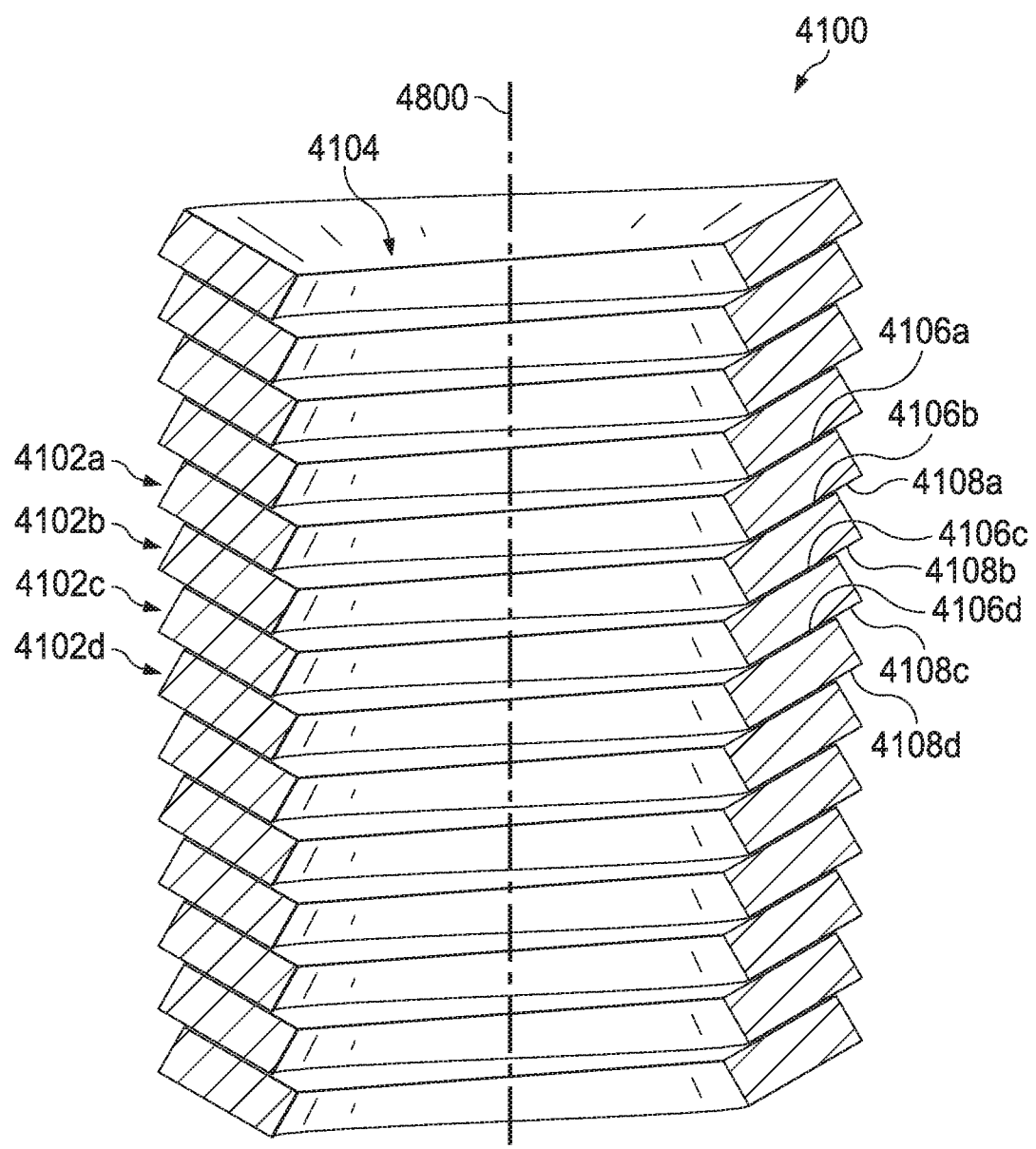
FIG. 4B illustrates a cross section of a spring hinge according to a specific example embodiment of the disclosure.

FIG. 4B depicts a cross sectional view of the spring hinge 4100 depicted in FIG. 4A. As depicted in FIG. 4B, the plurality of spirals 4102a, 4102b, 4102c, 4102d may have corresponding upper surfaces 4106a, 4106b, 4106c, 4106d and lower surfaces 4108a, 4108b, 4108c, 4108d. The upper surfaces 4106a, 4106b, 4106c, 4106d and lower surfaces 4108a, 4108b, 4108c, 4108d may have flat or planar cross-sectional profiles. The lengthwise axis 4800 of the spring hinge may be defined by the direction in which the central cavity 4104 runs. In some embodiments, the flat or planar surfaces of the upper surfaces 4106a, 4106b, 4106c, 4106d and the lower surfaces 4108a, 4108b, 4108c, 4018d may intersect the lengthwise axis 4800 of the spring hinge 4100 at an angle in the range of about 25 degrees to about 65 degrees. Preferably, the angle of intersection will be about 45 degrees.

The flat or planar surfaces of the upper surfaces 4106a, 4106b, 4106c, 4106d and the lower surfaces 4108a, 4108b, 4108c, 4108d may advantageously provide for a frictional contact between adjacent surfaces, such as between lower surface 4108a and upper surface 4106b or between lower surface 4108b and upper surface 4106c. The frictional contact may deter translational or shearing movement of the upper surfaces 4106a, 4106b, 4106c, 4106d with respect to the lower surfaces 4108a, 4108b, 4108c, 4108d. In use, the spring hinge 4100 may be bent or curved with little to no translational or shearing movement of the upper surfaces 4106a, 4106b, 4106c, 4106d with respect to the lower surfaces 4108a, 4108b, 4108c, 4108d.

The slanted orientation of the flat or planar surfaces of the upper surfaces 4106a, 4106b, 4106c, 4106d and the lower surfaces 4108a, 4108b, 4108c, 4108d may also advantageously deter or prevent translational or shearing movements of the upper surfaces 4106a, 4106b, 4106c, 4106d with respect to the lower surfaces 4108a, 4108b, 4108c, 4108d. The plurality of spirals 4102a, 4102b, 4102c, 4102d of spring hinge 4100 may be formed such that each spiral has a conic configuration. The layering of the plurality of spirals 4102a, 4102b, 4102c, 4102d with conic configurations may provide for a series of conical geometries that contour, are in contact, or nest against one another. When a translational force is applied to the spring hinge 4100, the nested flat surfaces provide resistance against translation movement of the upper surfaces 4106*a*, 4106*b*, 4106*c*, 4106*d* relative to the lower surfaces 4108*a*, 4108*b*, 4108*c*, 4108*d*. This arrangement therefore advantageously provides a hinge device with a dynamic axis of rotation that is substantially orthogonal to its lengthwise axis, while resisting translational or shearing movement of the spirals of the device relative to one another.

Figure 5A:
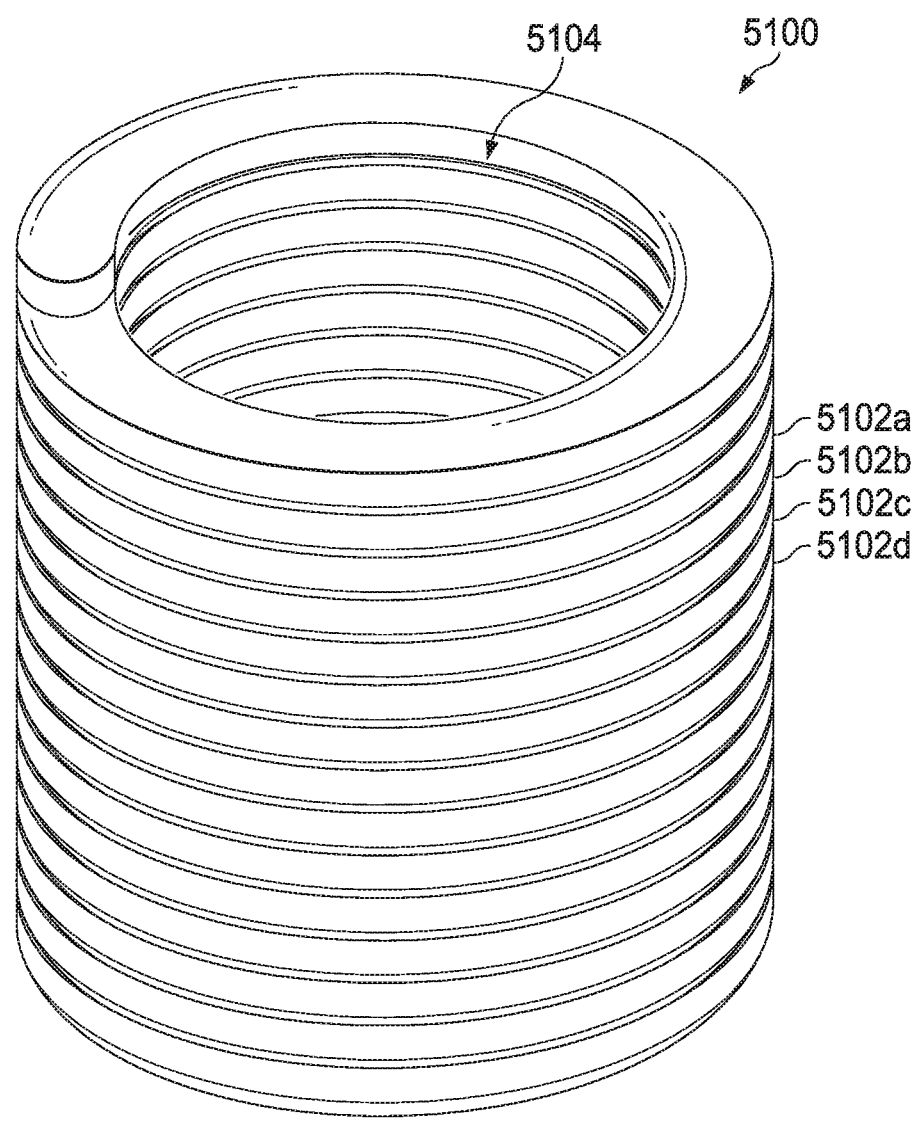
FIG. 5A illustrates a spring hinge according to a specific example embodiment of the disclosure.

FIG. 5A depicts embodiments of the present disclosure wherein the plurality of spirals 5102*a*, 5102*b*, 5102*c*, 5102*d* of the spring hinge 5100 are disposed about a lengthwise axis 5800 and have upper and lower surfaces with interlocking male and female features or geometries. For example, the plurality of spirals 5102*a*, 5102*b*, 5102*c*, 5102*d* may have a first surface with a convex profile in a first direction and a second surface with a concave profile in a second direction opposite to the first direction. A portion of the first surface with the convex profile may be configured to rest within or nest against an adjacent portion of the second surface with the concave profile when the coil spring of the spring hinge 5100 is in an unexpanded state. The male and female features, such as the convex profiles and concave profiles, may deter translational or shearing movement of the plurality of spirals of the coil spring, and stabilizes movement of the primary coil spring when moving from the unexpanded state to an expanded or resting state.

Figure 5B:
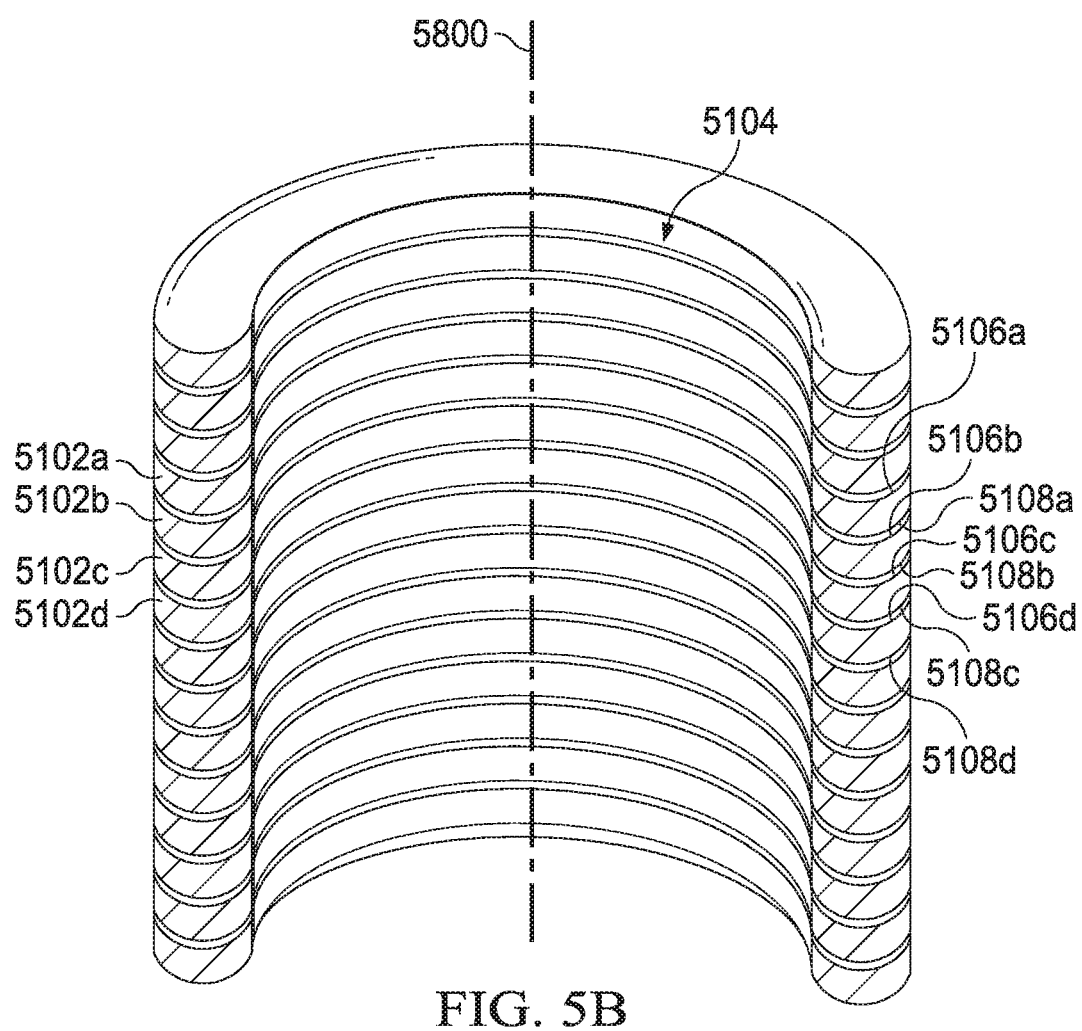
FIG. 5B illustrates a cross section of a spring hinge according to a specific example embodiment of the disclosure.

In FIG. 5B, a cross-sectional view of the embodiment of FIG. 5A is depicted. As shown in FIG. 5B, the plurality of spirals 5102*a*, 5102*b*, 5102*c*, 5102*d* may each have an upper surface 5106*a*, 5106*b*, 5106*c*, 5106*d* that is concave and a lower surface 5108*a*, 5108*b*, 5108*c*, 5108*d* that is convex. The configuration of FIG. 5B is depicted by way of example only, and the present disclosure encompasses other embodiments such as where the upper surfaces 5106*a*, 5106*b*, 5106*c*, 5106*d* are convex and the lower surfaces 5108*a*, 5108*b*, 5108*c*, 5108*d* are concave. Also, as shown in FIG. 5B is a lengthwise axis 5800 that runs through the central cavity 5104 of the spring hinge 5100.

The convex and concave orientations of the flat or planar surfaces of the upper surfaces 5106*a*, 5106*b*, 5106*c*, 5106*d* and the lower surfaces 5108*a*, 5108*b*, 5108*c*, 5108*d* may also advantageously deter or prevent translational or shearing movements of the upper surfaces 5106*a*, 5106*b*, 5106*c*, 5106*d* and the lower surfaces 5108*a*, 5108*b*, 5108*c*, 5108*d* relative to one another. The layering of the plurality of spirals 5102*a*, 5102*b*, 5102*c*, 5102*d* may provide for a series of convex and concave surfaces that are in contact or nest against one another. When a translational force is applied to the springe hinge 5100, a convex portion of a spiral would bias against a concave portion of another spiral, thus providing resistance against translation movement of the plurality of spirals 5102*a*, 5102*b*, 5102*c*, 5102*d*.

In some embodiments, the upper surfaces 5106*a*, 5106*b*, 5106*c*, 5106*d* and the lower surfaces 5108*a*, 5108*b*, 5108*c*, 5108*d* may have a radius of curvature of about 1-5 mm, preferably 2 mm. A smaller radius of curvature may promote greater stabilization of each spiral or layer against one another but may also increase difficulty in pivotal movement of the spring hinge 5100. A greater radius of curvature may be easier for manufacturing and provide for greater ease of pivotal movement but may not deter translational or shearing movement of spring hinge spirals with respect to one another as much as embodiments having a smaller radius of curvature.

Figure 6A:
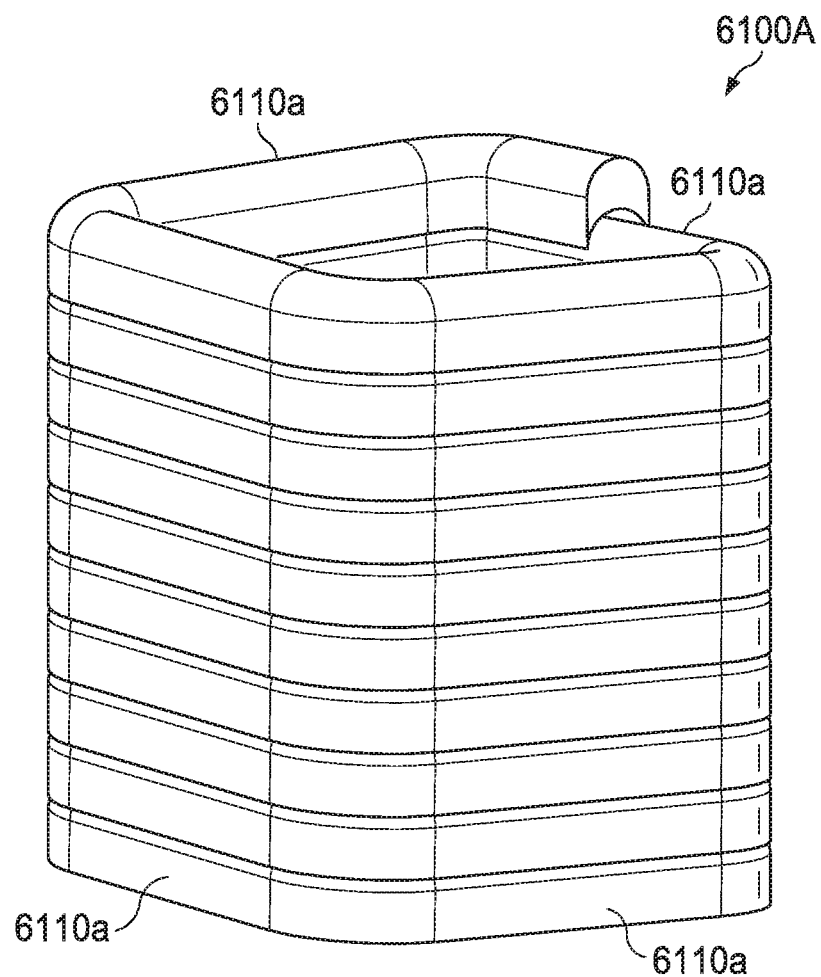
FIG. 6A illustrates a spring hinge according to a specific example embodiment of the disclosure.
Figure 6B:
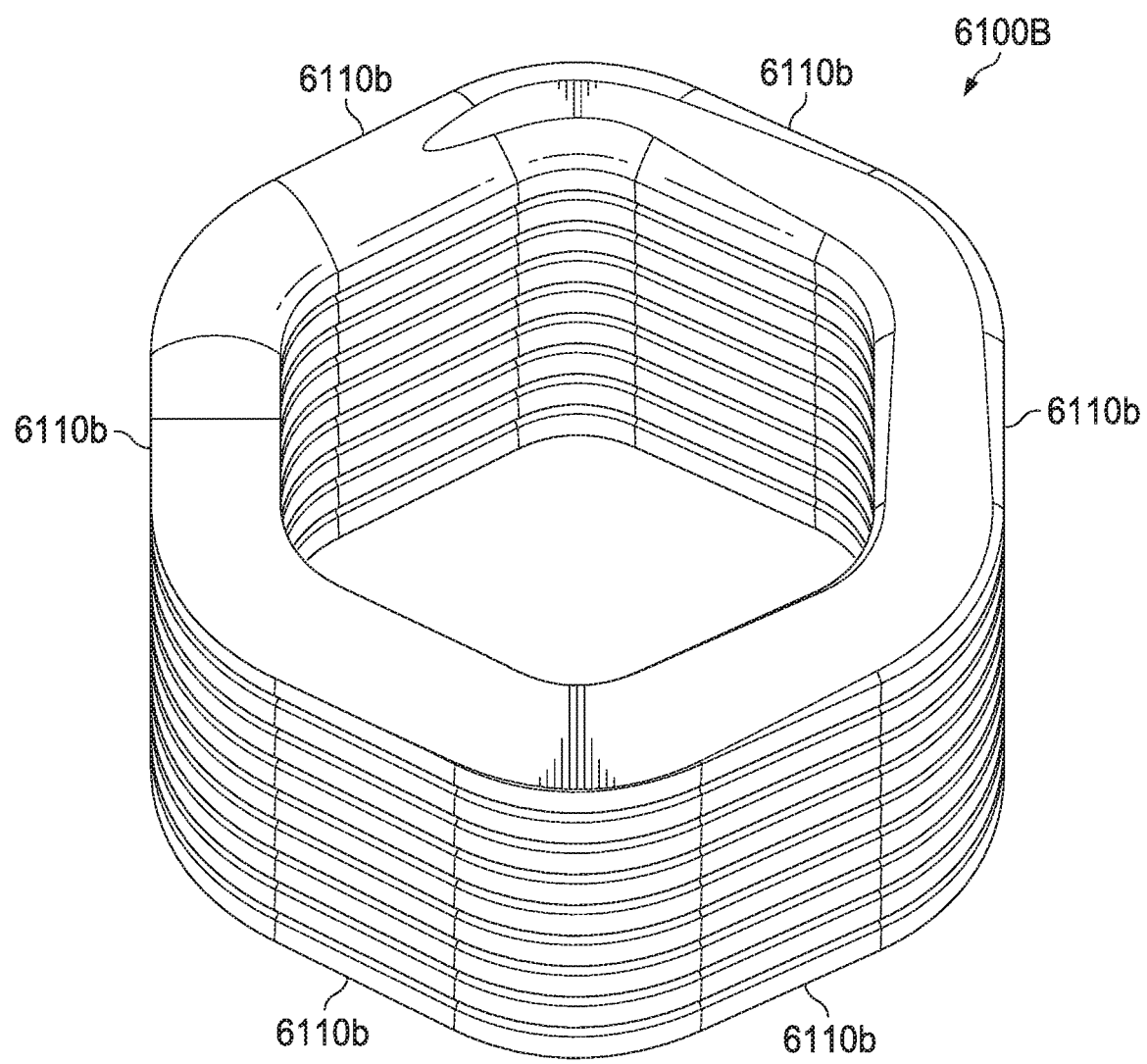
FIG. 6B illustrates a spring hinge according to a specific example embodiment of the disclosure.

FIG. 6A and FIG. 6B depict example embodiments of the present disclosure in which the coil spring forms a polygonal shape when viewed in a transverse plane. As shown in FIG. 6A, a coil spring of the spring hinge 6100A may comprise a square geometry or have a square profile in a cross section viewed along a traverse plane. Spring hinge 6100A may comprise four sides 6110*a*. The four sides 6110*a* may not join at sharp angles and may instead may merge curvilinearly with an adjacent side. In some embodiments, each of the four sides 6110*a* may have a length of about 20-30 mm, preferably about 25 mm.

As shown in FIG. 6B, a coil spring of the spring hinge 6100B may comprise a hexagonal geometry or have a hexagonal profile in a cross section along a traverse plane. Spring hinge 6100B may comprise six sides 6110*b*. The six sides 6110*b* may not join at sharp angles and may instead may merge curvilinearly with an adjacent side. In some embodiments, each of the six sides 6110*b* may have a length of about 20-30 mm, preferably about 25 mm.

The geometries of the spring hinges 6100A, 6100B formed by sides 6110*a*, 6110*b* may deter and/or provide resistance against translational or shearing movement of the upper and lower surfaces of the helical structure that make up the coil spring. When a translational force is applied to a side 6110*a*, 6110*b* of the springe hinge 6100A, 6100B, the translational force would be transferred to and at least partially absorbed by adjacent sides 6110*a*, 6110*b*. As a result, the plurality of sides 6110*a*, 6110*b* would advantageously provide for resistance against translational or shearing movement of the spirals of the spring hinge 6100A, 6100B.

The embodiments depicted in FIGS. 6A and 6B are provided by way of example only. In some embodiments, a spring hinge may have a circular, triangular, rectangular, pentagonal, hexagonal, or any polygonal geometry along a transverse plane.

Figure 6C:
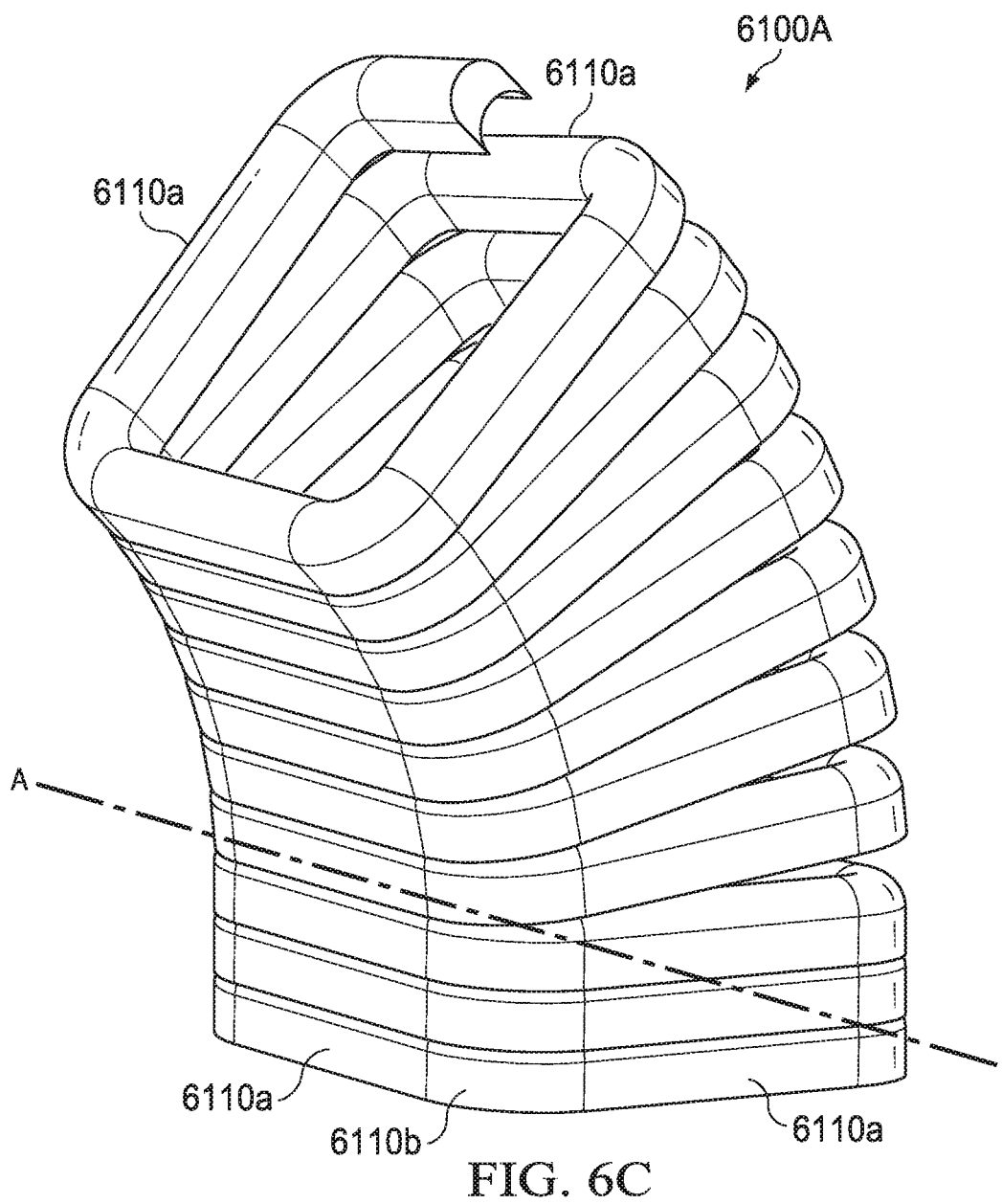
FIG. 6C illustrates another view of the spring hinge of FIG. 6A.

FIG. 6C depicts a view of a spring hinge 6100A in which the spring hinge has been pivoted along an axis A that is aligned with one of the sides 6110*a*. The sides 6110*a* tend to limit the direction of bending or deformation of the spring hinge 6100A. In the simple case of uniform spring material and cross-section, the resistance of the spring hinge 6100A to pivoting movement is least when the pivot axis is aligned with one of the sides 6110*a*, rather than one of the corners 6110*b*. As such, the axis of rotation of the spring hinge 6100A tends to be limited to a small number of axes that align with the sides 6110*a*. In other words, linear (e.g. as opposed to circular) spring sides provide increased stability of the pivoting of the spring's lengthwise axis (e.g. due to joint flexion) about a plane. This can have beneficial therapeutic effects since the axis of rotation of the coil spring can be better aligned with an anatomical axis of the patient. As an additional feature, the geometry of the spring coils (spirals) along a transverse plane (e.g., polygonal in FIGS. 6A and 6B) may not be constant along the length of the spring (as shown in FIGS. 6A and 6B) but may vary along the length of the spring coil. For example, the spring coil profiles could be slightly rotated instances of the same base geometry, thus guiding the spring to bend along a dynamic axis of rotation depending on the degree to which the lengthwise axis of the spring is bent or deformed.

Coil springs with non-circular profiles, such as the polygonally-profiled coil springs of FIGS. 6A and 6B, may also result in pivot rotation axes (e.g. axes often, but not necessarily, substantially orthogonal to the lengthwise axis of the spring coil) with non-isotropic pivoting resistance. In other words, the force necessary to bend or deform the lengthwise axis of the coil spring may be greater or lesser depending on the direction of bending or deformation.

Specifically, the radius of the spiral profile, defined relative to the coil spring lengthwise axis, may affect the pivoting resistance. For example, in the case of a spiral of substantially uniform material and cross-section (e.g. the spirals shown in FIGS. 6A and 6B), the directions corresponding to the portions of the spiral with the largest radius relative to the lengthwise axis of the coil spring (e.g. the "corners" of the polygonal spirals in FIGS. 6A and 6B) will present the greatest pivotal resistance. As a consequence, the directions corresponding to the spiral portions with the least radius relative to the lengthwise axis (e.g. the "sides" of the polygonal spirals in FIGS. 6A and 6B) will be easiest (i.e. require the least force) to bend or deform the coil spring along. Further, bending or pivoting the coil spring in a direction of a relatively greater pivotal resistance (e.g. corresponding to a direction of a spiral portion with relatively larger radius, such as a "corner" of a polygon), may be generally unstable and result in the direction of bending motion "converging" to a relatively stable direction with relatively lesser pivotal resistance (e.g. corresponding to a direction of a spiral portion with relatively lesser radius, such as a "side" of a polygon). In this way, spring hinges can "guide" and/or substantially limit the direction of bending, depending at least in part on the transverse geometry (profile) of the coil spiral.

In the simple case of uniform spiral material and cross-section, the anisotropy of pivot resistance is due to the fact that bending or deforming the spring coil in the directions corresponding to the spiral portions with relatively large spiral radius requires the entire spring coil to bend at a larger radius of curvature (due to the compressed and thus substantially rigid spiral material on the inside of the curve assumed by the bent spring), thus requiring the coil spring to be stressed such that its lengthwise axis becomes a relatively larger curve for a given desired spring angle between the spring endpoints (e.g. 90 degrees).

However, it is also understood that spring coils may comprise non-uniform spiral material and/or cross section, which may further influence pivot resistance anisotropy or lack thereof for coil springs with non-circular profiles. For example, if the spiral portions of relatively larger radius have a thinner cross-section or are composed of a more compressible material relative to the spiral portions with relatively smaller radius, then the pivot resistance in the direction of the spiral portions of relatively larger radius may actually be equal to or even less than the pivot resistance in the directions corresponding to spiral portions with relatively small radius. In other words, factors affecting pivot resistance in various directions include spiral portion radius (relative to the spring coil lengthwise axis), material, and cross section.

Figure 7A:
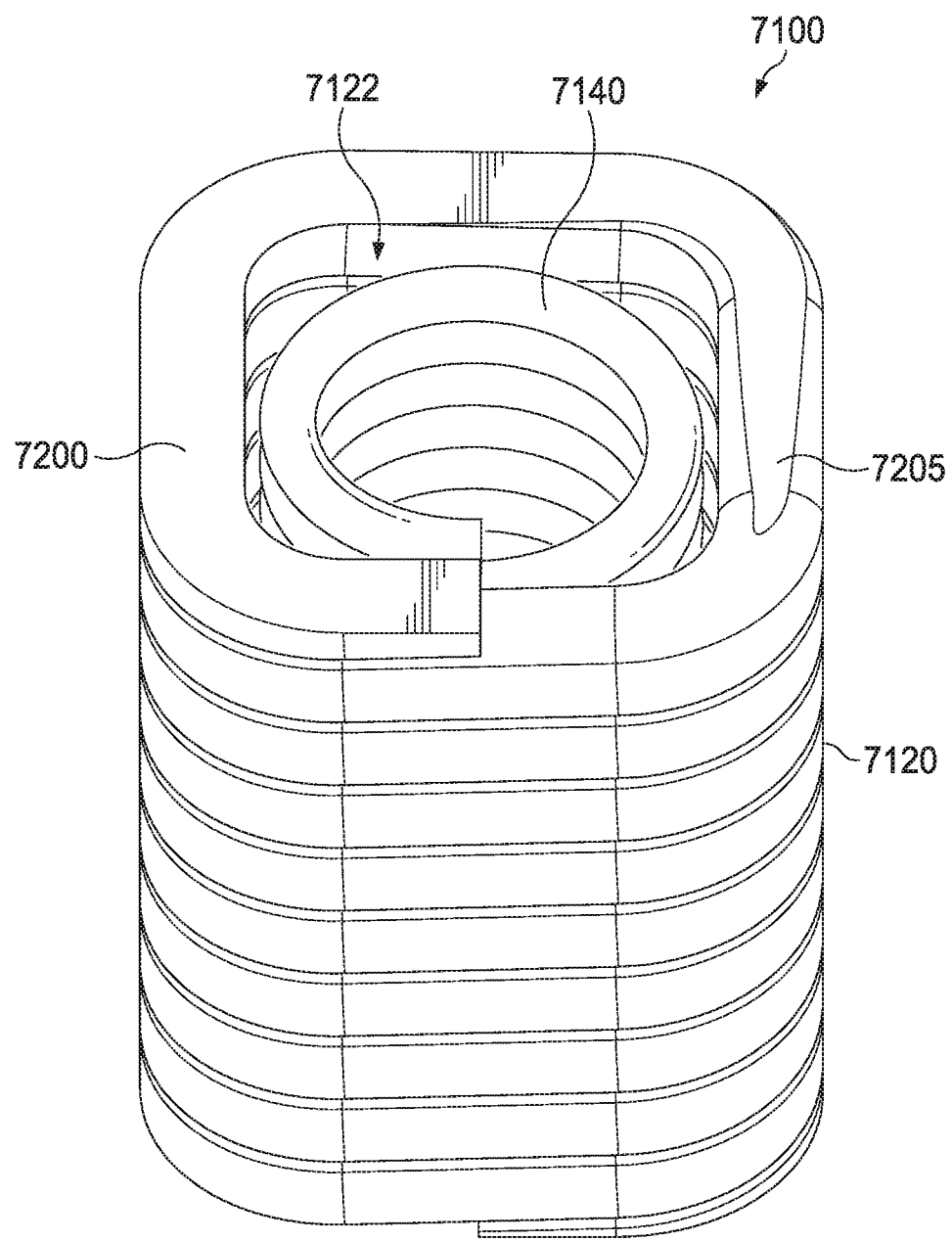
FIG. 7A illustrates a spring hinge according to a specific example embodiment of the disclosure.

As depicted in FIG. 7A, in some embodiments of the present disclosure, a spring hinge 7100 may comprise both a primary coil spring 7120 and a secondary coil spring 7140. In some embodiments, the secondary coil spring 7140 may be disposed within a central cavity 7122 of the primary coil spring 7120. The secondary coil spring 7140 may be sized so as to be inserted into or fit within the central cavity 7122. For example, the secondary coil spring 7140 may have an outer width that is smaller than the inner width of the central cavity 7122 and may have a length similar to or less than a length of the central cavity 7122 or a length of primary coil spring 7120. In other embodiments, the secondary coil spring 7140 may have a length exceeding the length of the primary coil spring 7120. The secondary coil spring 7140 may be positioned such that the secondary coil spring 7140 and the primary coil spring 7120 are concentric with one another. The secondary coil spring 7140 and the primary coil spring 7120 may share the same lengthwise axis. Also shown in FIG. 7A is a flat 7200 found on the upper surface of the primary coil spring 7120. The flat 7200 is aligned with a plane that is orthogonal to the lengthwise axis of the spring hinge 7200. As such, the flat 7200 tapers to a narrow point 7205 as the underlying spiral follows its helical path. The flat 7200 therefore provides a uniform, orthogonal surface for mating with an end cap (see FIG. 8A).

Figure 7B:
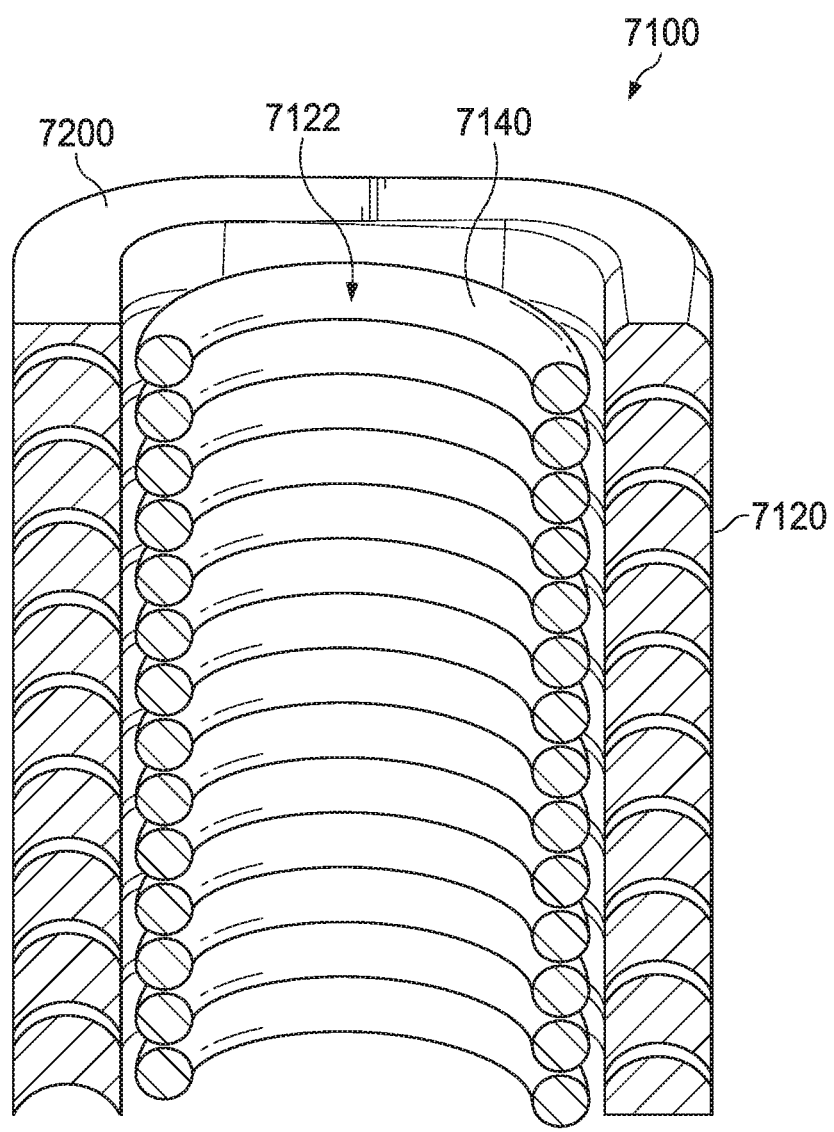
FIG. 7B illustrates a cross section of a spring hinge according to a specific example embodiment of the disclosure.

In FIG. 7B, a cross-sectional view of the embodiment of FIG. 6A is depicted. As shown in FIG. 7B, the primary coil spring 7120 may have spirals with complementary cross sections (e.g., concave and convex) that nest against one another in order to deter translational or shearing movement of the spirals, as described in regard to FIGS. 5A, 5B, 6A, and 6B. Also shown in FIG. 7B is a flat 7200 found on the upper surface of the primary coil spring 7120 that provides a uniform, orthogonal surface for mating with an end cap (see FIG. 8A).

In some embodiments, the secondary coil spring 7140 may be a circular coil. The primary coil spring 7120 may deter translational or shearing movement of the spring hinge 7100 layers with respect to one another and may further guide the bending or deformation of the secondary coil spring 7140 when moving from the unexpanded state to an expanded state (e.g., as described in regards to FIGS. 6A, 6B, and 6C). The primary coil spring 7120 may serve to deter translational or shearing movement of the secondary coil spring 7140 while providing minimal resistance to pivotal movement or stretching of the secondary coil spring 7120 along a desired axis of rotation. In use, an external fixation system utilizing the spring hinge 7100 may advantageously allow a patient to bend an anatomical joint without risking unwanted or unstable translational or shearing movement.

In some embodiments, the primary coil spring 7120 may have a positive spring constant; that is, it may resist bending or deformation of its lengthwise axis. In other embodiments, the primary coil spring 7120 may have a zero-spring constant (e.g., unattached spirals or rings held in place by ends pieces, merely to deter translational or shearing movement and guide the bending or deformation of the secondary coil spring 7140), or even a negative spring constant (e.g., primary coil spring 7120 applies force to end pieces in a resting state).

In some embodiments, the central cavity 7122 of the primary coil spring 7120 may have a diameter or a width of about 13-15 mm, but can have a diameter or a width of about 5-25 mm. The diameter or width of the central cavity 7122 may be sized to receive the secondary coil spring 7140. The secondary coil spring 7140 may have a diameter or a width of about 12-14 mm, but can have a diameter or a width of about 5-25 mm. The primary coil spring 7120 may have a length of about 25-30 mm (but can have a length of about 15-50 mm), and the secondary coil spring 7140 may have a length of about 25-30 mm (but can have a length of about 15-50 mm).

The secondary coil spring 7140 may have a spring constant of about 10-20 lb/in. Further, the secondary coil spring 7140 may be comprised of materials such as various polymers or metals. Some suitable materials for the secondary coil spring 7140 include but are not limited to spring-tempered steel, piano steel wire, 302 stainless steel, and/or other resilient materials. In addition to the materials used for the secondary coil spring 7140, the primary coil spring 7120 could comprise any pliable material or component. The primary coil spring 7120 may have a spring constant of about 0.5-5.0 lb/in.

Embodiments of the present disclosure may provide for external fixation systems wherein a spring hinge is secured to an end cap. An example embodiment of an end cap 8200 is depicted in FIG. 8A. The end cap 8200 may comprise a plurality of threads 8202, which may be used to secure either a primary coil spring or a secondary coil spring of the spring hinge. For example, two end caps 8200 may be used to secure a primary coil spring at either end, with the plurality of threads 8202 secured or threaded into the inner helical surface of the plurality of spirals of the primary coil spring. In other embodiments, two end caps 8200 may be used to secure a secondary coil spring at either end, with the plurality of threads 8202 secured or threaded into the inner helical surface of the plurality of spirals of the secondary coil spring. In such embodiments, the primary coil spring may be disposed around the secondary coil spring and may not be secured against the plurality of threads 8202.

The end cap 8200 may also comprise a first flange 8204. The first flange may be an annular protrusion with a diameter greater than a diameter of the plurality of threads 8202. Preferably, the first flange may include a flat surface that may mate with a flat surface on the primary coil spring or the secondary coil spring, such as the flat 7200 depicted in FIGS. 7A and 7B. In some embodiments, the first flanges 8204 of two end caps 8200 may serve to secure a primary coil spring therebetween. For example, a secondary coil spring 8140 may be secured at either end to the plurality of threads 8202 of an end cap 8200. A primary coil spring 8120 that surrounds the secondary coil spring 8140 may be secured by the first flanges 8204 of each of the end caps 8200. The first flanges 8204 may prevent the primary coil spring from slipping or otherwise sliding off. For example, the first flanges 8204 may have a radius large enough to make contact with flats at the ends of the primary coil spring 8120. The distance between the inner surface of the first flanges (i.e., the surface facing primary and secondary spring coils 8120, 8140) when the end caps are threadably secured to a secondary spring coil 8140 may be such that the primary spring coil 8120 is compressed between the end caps 8204, thus creating a frictional force between the end caps and primary spring coil 8120 that secures the primary spring coil 8120 around the secondary spring coil 8140.

Figure 8B:
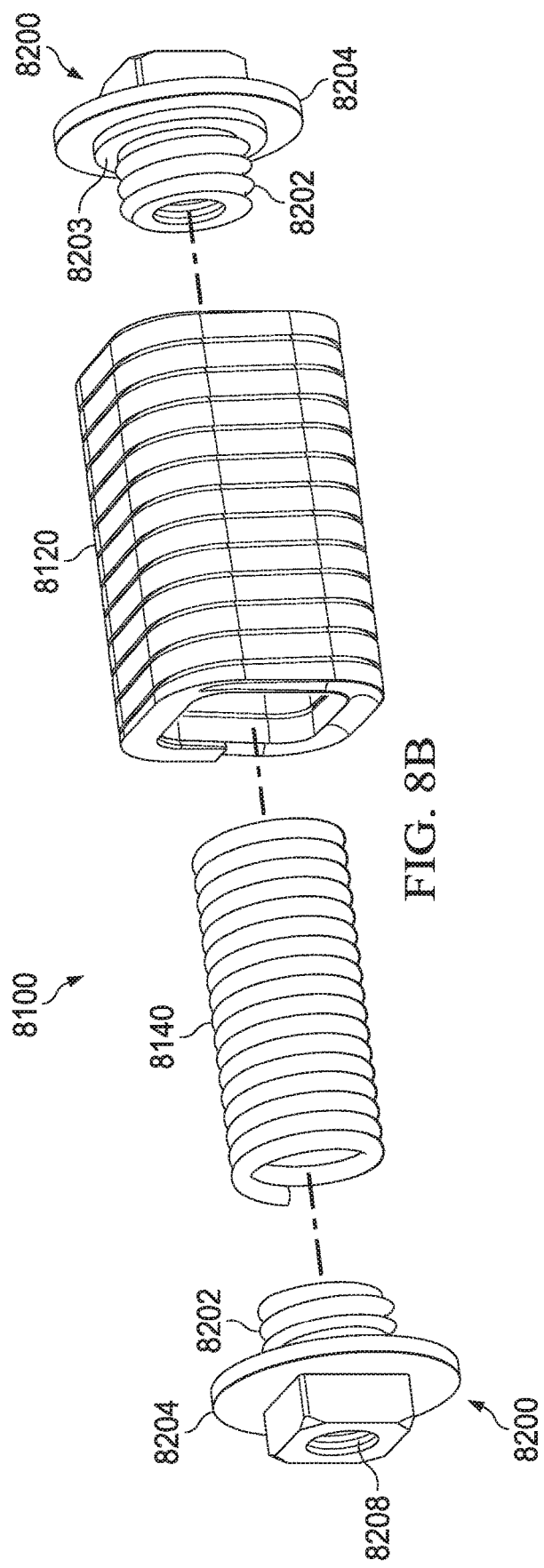
FIG. 8B illustrates a portion of an external fixation system according to a specific example embodiment of the disclosure.

The end cap 8200 may further comprise a second flange 8203 disposed on and protruding from the first flange 8204. The second flange 8203 may serve to maintain a centered positioning of the primary coil spring 8120 about the secondary coil spring 8140. The second flange 8203 may have a circular profile (as illustrated in FIG. 8A) or a non-circular profile. A second flange with a non-circular profile may maintain the rotational orientation of a non-circular primary spring coil (e.g. as shown in FIG. 8B) about the secondary coil spring. On the other hand, a second flange 8203 with a circular profile may allow the primary coil spring (which may form square or hex spiral profile) to rotate and self-align. The ability of the primary coil spring to self-align accommodates for slight misalignment of more than one hinge (e.g. a hinge pair) disposed between two external supports during hinge installation by surgeons, which may be advantageous due to the difficulty of hinge alignment during surgery.

The end cap 8200 may further comprise a securing feature 8206. The securing feature 8206 may secure the end cap 8200 to an external fixation system. For example, the securing feature may comprise internal threads 8208 or other fastening means to be secured, directly or indirectly, to a portion of an external fixation system, such as a threaded rod.

Figure 8C:
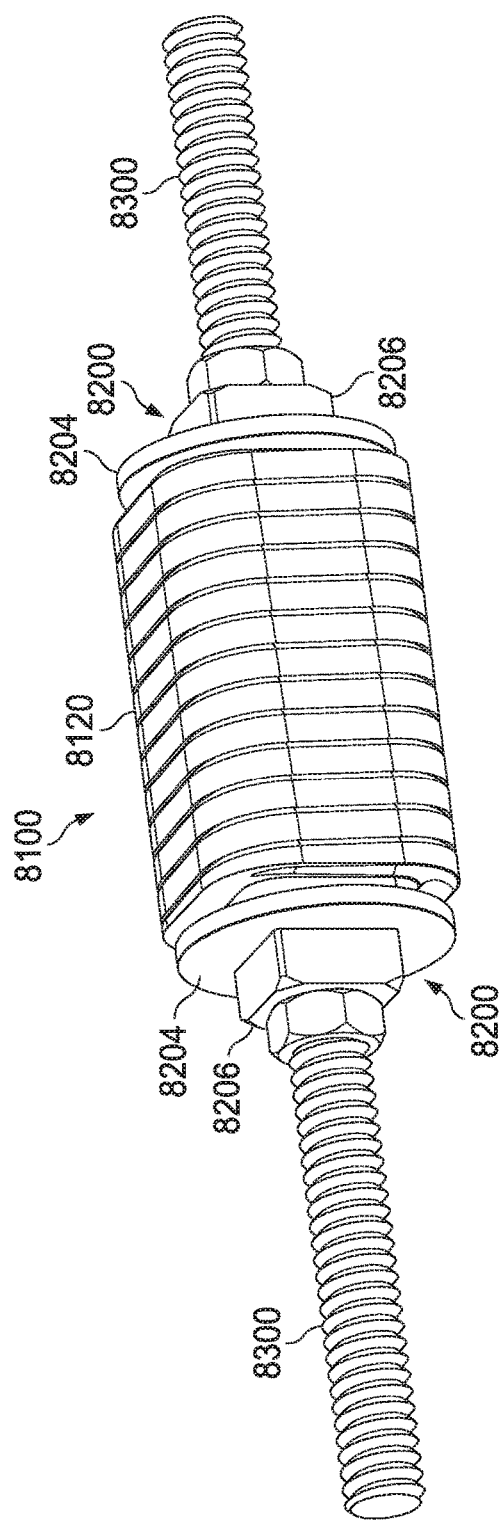
FIG. 8C illustrates a portion of an external fixation system according to a specific example embodiment of the disclosure.

An exemplary embodiment of a device is depicted in FIG. 8B and FIG. 8C, wherein two end caps 8200 are used to secure a spring hinge 8100. FIG. 8B is an exploded view of the device, and FIG. 8C is an assembled view of the device. The plurality of threads 8202 of the two end caps 8200 may be used to secure an internal secondary coil spring 8140 at either end. An outer primary coil spring 8120 may fit over the secondary coil spring 8140 like a sleeve. The first flanges 8204 of the two end caps 8200 may secure the primary coil spring 8120 in its position and prevent the primary coil spring 8120 from sliding off or becoming otherwise separated from the spring hinge 8100. As depicted, securing features 8206 may be further secured or fastened to other components, such as threaded rods 8300 of an external fixation system.

The device 8100 illustrated in FIGS. 8B and 8C may be assembled by inserting the secondary coil spring 8140 into the primary coil spring 8120. Then, the secondary coil spring 8140 may be threadably coupled (e.g., screwed) to the end caps 8200, e.g., by hand or by the use of an end cap manipulation tool (e.g., a general-purpose device such as a wrench or a special-purpose tool adapted for the end caps). The end caps insertion into and/or tightening with respect to the secondary coil spring 8140 may or may not frictionally secure the primary coil spring 8120 between the end caps (e.g., to prevent sliding about the lengthwise axis of the secondary coil spring 8140). Additionally, securing tabs or hooks may protrude from the inside of the end cap surface in order to prevent rotation of the primary coil spring 8120. Once assembled, the device 8100 can provide the benefits of FIGS. 7A, 7B, and 7C to an external fixator to which the device 8100 is attached via threaded rods 8300 threadably coupled to the internal threads 8208 of the end caps 8200.

In some embodiments, the primary coil spring 8120 and the secondary coil spring 8140 may be coiled in opposite directions (i.e. have opposite "directions of wind") in order to enhance planar stability of the secondary coil spring's lengthwise axis during pivoting (e.g. due to joint bending and/or flexion), which may be required in some clinical cases. Opposite coiling of the primary coil spring 8120 and the secondary coil spring 8140 may prevent intertwining or enmeshing of the spirals of the primary coil spring 8120 and the secondary coil spring 8140.

In some embodiments, the plurality of threads 8202 may have a length of about 3-6 mm. The securing feature 8206 may have a length of about 5-7 mm. The first flange may have a width or a diameter of about 22-25 mm, but can have a width or diameter of about 15-30 mm.

Figure 9A:
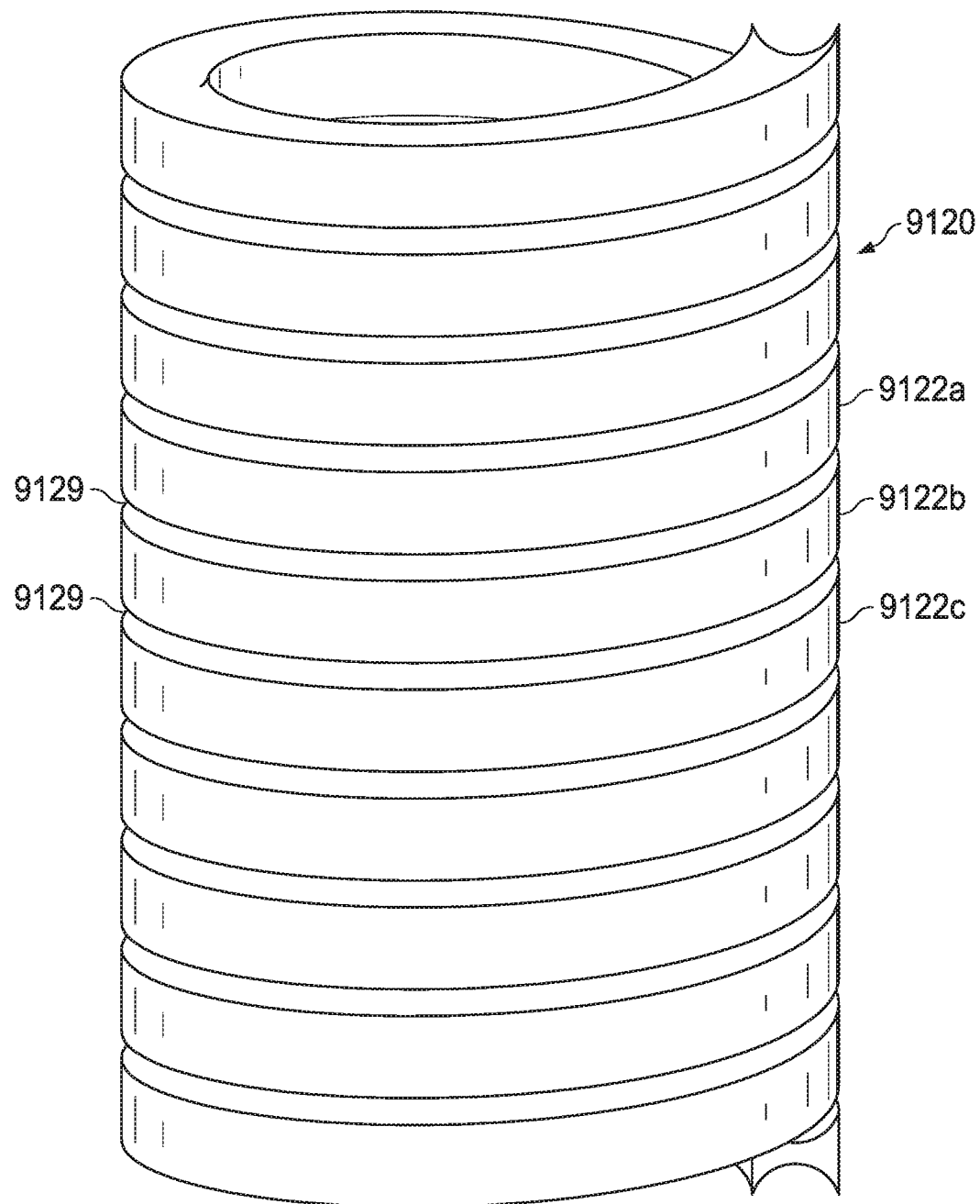
FIG. 9A illustrates a primary coil spring according to a specific example embodiment of the disclosure.

FIG. 9A depicts a primary coil spring 9120 according to some embodiments of the present disclosure. A primary coil spring 9120 may have a helical structure that comprises a plurality of spirals 9122a, 9122b, 9122c. Each of the plurality of spirals 9122a, 9122b, 9122c may merge curvilinearly into one or more adjacent spirals. In some embodiments, the upper and lower surfaces of the plurality of spirals 9122a, 9122b, 9122c of the primary coil spring 9120 may not be in contact with a spiral above or below it. In such embodiments, the primary coil spring 9120 may have a gap between each pair of spirals or layers of the coil. For example, an interstitial gap 9129 may be disposed between spirals 9122a, 9122b. Similarly, an interstitial gap 9129 may be disposed between spirals 9122b, 9122c.

Figure 9B:
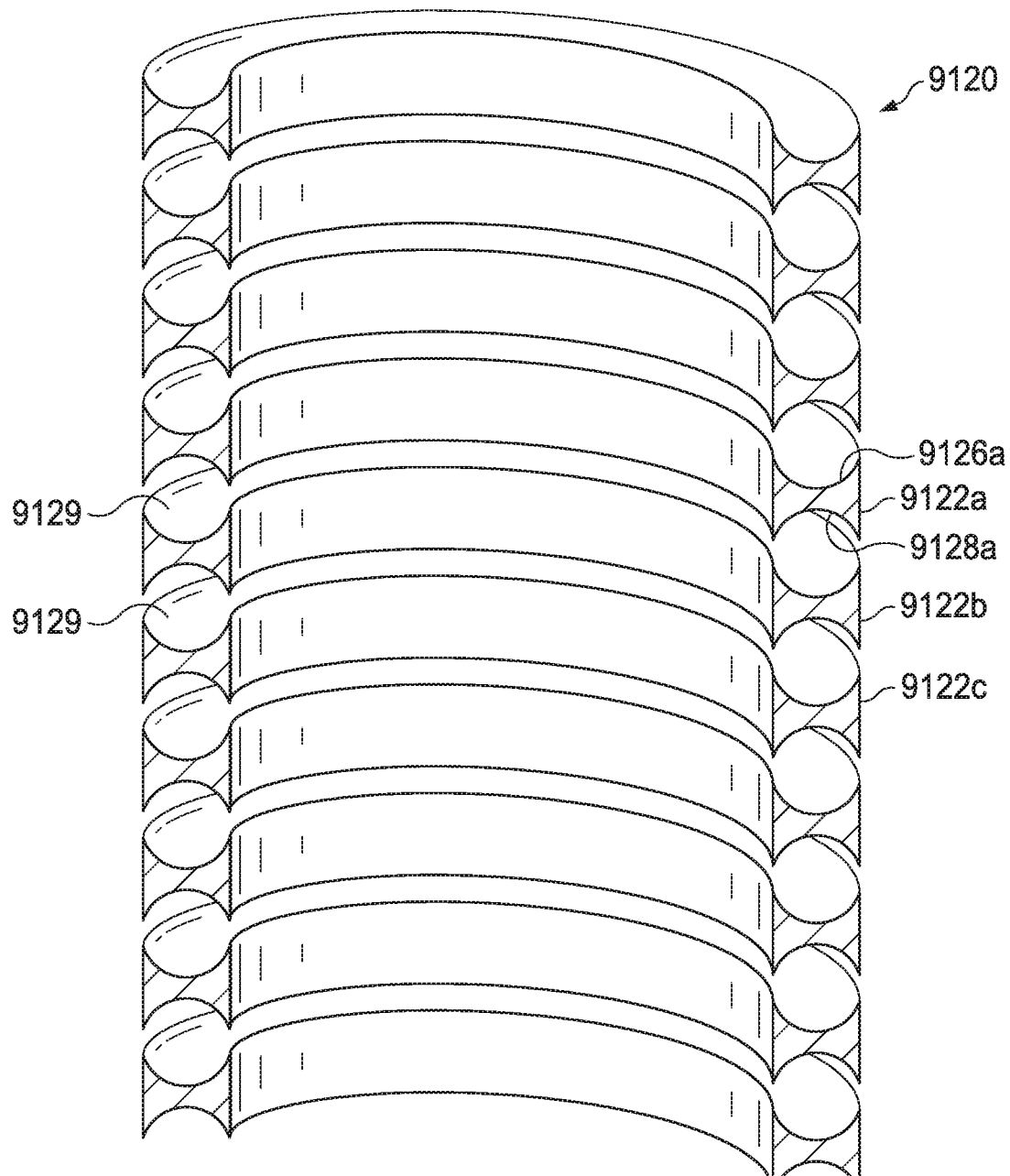
FIG. 9B illustrates a cross section of a primary coil spring according to a specific example embodiment of the disclosure.

FIG. 9B depicts a cross section of the primary coil spring 9120. The plurality of spirals 9122a, 9122b, 9122c of the primary coil spring 9120 may be formed such that an upper surface 9126*a* and a lower surface 9128*a* of a spiral each have a concave configuration or a concave surface. As a result, the interstitial gap 9129 between each of the spirals may have a circular profile. The interstitial gap 9129 may be sized and configured to receive a spacer element, such as an interstitial coil spring 9160.

Figure 9C:
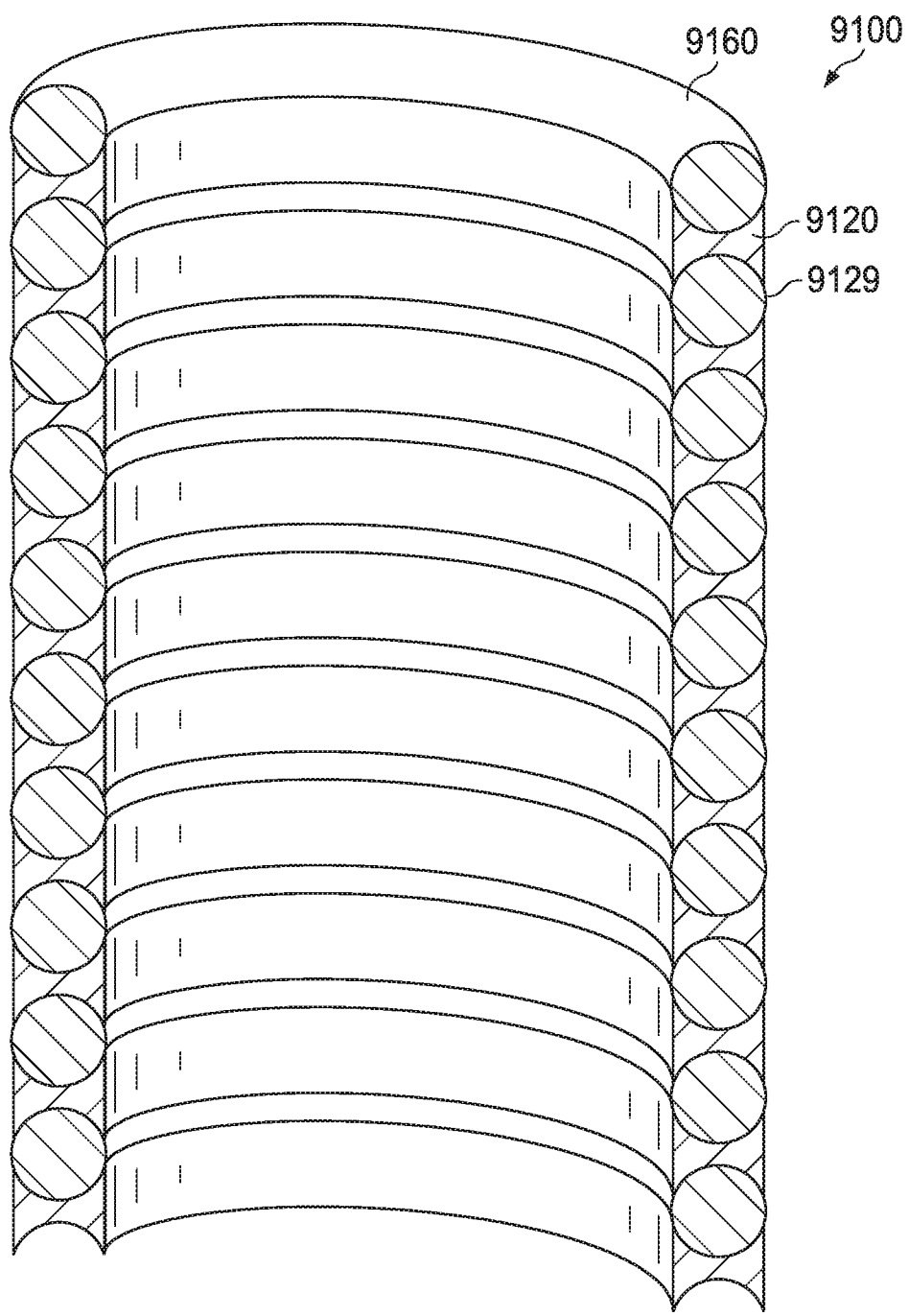
FIG. 9C illustrates a spring hinge according to a specific example embodiment of the disclosure.

As depicted in FIG. 9C, an interstitial coil spring 9160 may be threaded through the interstitial gap 9129 of the primary coil spring 9120. Disposing an interstitial coil spring 9160 between the plurality of spirals of the primary coil spring 9120 may serve to deter translational or shearing movement of the plurality of spirals of the primary coil spring, and may serve to stabilize movement of the primary coil spring 9120 when moving from the unexpanded state to an expanded state. When a translational force is applied to spring hinge 9100, the threading of the interstitial coil spring 9160 in the interstitial gap 9129 of the primary coil spring 9120 serves to deter translational or shearing movement and serves to stabilizes the translational position of the spring hinge 9100. The interstitial coil spring 9160 may deter translational or shearing movement by providing a frictional obstacle for the plurality of spirals of the primary coil spring 9120 to overcome when a translational force is applied. For instance, if a translational force is applied to one spiral 9122*b* of the primary coil spring 9120, but not to an above or below spiral 9122*a*, 9122*c*, the spiral 9122*b* with the translational force applied would transfer the force to an interstitial coil spring 9160, which would subsequently transfer the force in the same direction. However, if the above and/or below spirals 9122*a*, 9122*c* did not experience the originally applied translational force, the above and/or below spirals 9122*a*, 9122*c* would present a counteracting force to the interstitial coil spring due to the connection between adjacent spirals 9122*a*, 9122*b*, 9122*c* of the primary coil spring 9120, and the generally rigid and/or resilient material of the primary coil spring 9120. Thus, an interstitially disposed coil spring 9160 facilitates consistent alignment of the spirals of the primary coil spring 9120 along the lengthwise axis of the primary coil spring.

The radius of curvature of the interstitial gap 9129 of the primary coil spring 9120 and the spiral cross section of the interstitial coil spring 9160 may affect the resistance to translational shearing of the spirals of the primary coil spring 9120. For example, a larger radius of curvature may provide more resistance to translational movement (e.g. due to larger frictional surfaces of the interstitial gap 9129 and interstitial coil spring 9160 to counteract the translational movement), whereas a smaller radius of curvature may provide less resistance to translational movement (e,g, for opposite reasons). Further, note that the radius of curvature of the interstitial gap 9129 of the primary coil spring 9120 and the interstitial coil spring 9160 may not be identical. In some embodiments, the radius of curvature of the interstitial gap 9129 of the primary coil spring 9120 may be approximately 1-5 mm, e.g. 2 mm. In some embodiments, the radius of curvature of the interstitial coil spring 9160 may be approximately 1-5 mm, e.g. 2 mm.

In some embodiments, the interstitial gap 9129 may have a thickness of about 1-3 mm, e.g. 1.6 mm. The interstitial coil spring 9160 may have a spring constant of about 10-20 lb/in. Further, the interstitial coil spring 9160 may be comprised of materials such as various polymers or metals. Some suitable materials for the interstitial coil spring 9160 include but are not limited to spring-tempered steel, piano steel wire, 302 stainless steel, and/or other resilient materials.

The embodiments depicted in the accompanying figures and described herein are provided by way of example only. Other embodiments are also within the scope of the present disclosure. For example, other embodiments may comprise a spring hinge, and the lengthwise axis thereof, that is formed in a curved configuration in its resting position. Such a spring may incorporate any of the above described features. For example, a curved spring may comprise spirals with particular geometries or upper and lower surfaces to deter translation or shearing movement. A curved spring may also be formed to have a transverse profile having multiple sides, such as a rectangular geometry. A curved spring may also be formed to have a secondary coil spring disposed within its central cavity, which may serve to resist translational or shearing forces applied to the curved spring. A curved spring may also be formed to have an interstitial gap between its spirals so that an interstitial coil spring may be threaded therethrough.

A curved spring may offer various advantages or be suitable for particular usages. For example, a curved spring may be more suitable in circumstances where the upper and lower external fixators are not parallel to one another or are secured at angles where a linear spring may not be conveniently installed or secured between said external fixators.

A curved spring may also help secure an anatomical joint in a particular position, such as a bent position. In use, a patient may then apply a pivotal force to bend the curved spring to a linear configuration. Such application may, for example, help with strength training of an anatomical joint or recovery of a particular range of motion about an anatomical joint.

Embodiments of the present disclosure may also provide for external fixation systems with a spring hinge that bends or curves upon exposure to different stimuli. For example, a spring hinge according to the present disclosure may be configured to bend or straighten upon exposure to higher or lower temperatures. A spring hinge according to the present disclosure may be configured to bend or straighten upon exposure to an electrical current. Such embodiments may allow for controlled pivotal movement of an external fixation system, and consequently a corresponding anatomical joint, without the need for a patient to apply force.

In use, an external fixation system may be secured about an anatomical joint of a patient. By using external stimuli, such as a higher temperature or electrical stimulation, a spring hinge of the external fixation system may exhibit pivotal motion, such as bending or straightening, without need or reducing the need for the patient to apply a force. Thus, motion may be introduced to the patient's anatomical joint with reduced effort from the patient. Further, due to a potential gap between spring hinge spirals, spring-based hinges may provide a dynamization effect on newly formed bone during deformity correction. In addition, the resilience of spring hinges can serve as a shock absorber for the joints in order to preserve a pathological articulating surface from being overloaded during weight-bearing and/or joint movements.

As will be understood by those skilled in the art who have the benefit of the instant disclosure, other equivalent or alternative devices, methods, and systems for orthopedic hinges can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of orthopedic hinges may be varied. In some embodiments, the size of a device and/or system may be scaled up (e.g., to be used for adult subjects) or down (e.g., to be used for juvenile subjects) to suit the needs and/or desires of a practitioner. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed devices, systems, and/or methods may exclude any other features or steps beyond those disclosed herein.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The title, abstract, background, and headings are provided in compliance with regulations and/or for the convenience of the reader. They include no admissions as to the scope and content of prior art and no limitations applicable to all disclosed embodiments.

The invention claimed is:

1. A spring hinge for an external fixation system, comprising:
 a coil spring having a helical structure with a central cavity extending along a central lengthwise axis, wherein the coil spring comprises a plurality of spirals having a non-circular cross-sectional shape in a plane in which the central lengthwise axis is disposed, the coil spring including a first end and a second end;
 a first end cap configured to couple to the first end of the coil spring and including a first portion configured to mount the first end cap to the external fixation system; and
 a second end cap configured to couple to the second end of the coil spring and including a second portion configured to mount the second end cap to the external fixation system;
 the coil spring comprising a first surface extending along a length of the coil spring and facing a first direction and an opposing second surface extending along the length of the coil spring and facing a second direction opposite the first direction, wherein a portion of the first surface is configured to abut a portion of the second surface when the coil spring is in an unexpanded resting state;
 wherein the first surface and the second surface are shaped to deter sheering movement between adjacent spirals of the plurality of spirals while permitting angular bending of the coil spring.

2. The spring hinge of claim 1, wherein the first surface is substantially flat in cross-section and the second surface is substantially flat in cross-section.

3. The spring hinge of claim 2, wherein the first surface frictionally engages the second surface when the coil spring is in the unexpanded resting state.

4. The spring hinge of claim 3, wherein the frictional engagement of the first surface and the second surface deters sheering movement between adjacent spirals of the plurality of spirals.

5. The spring hinge of claim 4, wherein the spring hinge further comprises a secondary coil spring disposed within the central cavity of the coil spring, wherein the secondary coil spring deters sheering movement between adjacent spirals.

6. The spring hinge of claim 2, wherein each spiral of the plurality of spirals has a flat, slanted profile in cross-section, and wherein the flat, slanted profile deters sheering between adjacent spirals when moving from the unexpanded state to an expanded state.

7. The spring hinge of claim 6, wherein the coil spring has a spring constant of about 0.5-5.0 lb/in.

8. The spring hinge of claim 6, wherein the spring hinge further comprises a secondary coil spring disposed within the central cavity of the coil spring, wherein the secondary coil spring deters sheering movement between adjacent spirals.

9. The spring hinge of claim 8, wherein the coil spring and the secondary coil spring each have a length of about 15 to 50 mm.

10. The spring hinge of claim 6, wherein a cross section of the coil spring along a transverse plane comprises a geometry selected from the group consisting of a rectangle, pentagon, and a hexagon.

11. A spring hinge for an external fixation system, comprising:
 a coil spring having a helical structure with a central cavity, wherein the coil spring comprises a plurality of spirals having a non-circular cross-sectional shape, the coil spring including a first end and a second end, wherein each spiral has a conical configuration such that a first spiral of the plurality of spirals nests at least partially within a second spiral of the plurality of spirals;

a first end cap configured to couple to the first end of the coil spring and including a first portion configured to mount the first end cap to the external fixation system; and a second end cap configured to couple to the second end of the coil spring and including a second portion configured to mount the second end cap to the external fixation system;

the coil spring comprising a first surface extending along a length of the coil spring and facing a first direction and an opposing second surface extending along the length of the coil spring and facing a second direction opposite the first direction, wherein a portion of the first surface is configured to abut a portion of the second surface when the coil spring is in an unexpanded resting state;

wherein the first surface and the second surface are shaped to deter sheering movement between adjacent spirals of the plurality of spirals while permitting angular bending of the coil spring.

12. The spring hinge of claim 11, wherein the second spiral confines at least a portion of the first spiral to deter sheering between the first spiral and the second spiral.

13. A spring hinge for an external fixation system, comprising:
a coil spring having a helical structure with a central cavity, wherein the coil spring comprises a plurality of spirals having a non-circular cross-sectional shape, the coil spring including a first end and a second end;
a first end cap configured to couple to the first end of the coil spring and including a first portion configured to mount the first end cap to the external fixation system; and
a second end cap configured to couple to the second end of the coil spring and including a second portion configured to mount the second end cap to the external fixation system;
the coil spring comprising a first surface extending along a length of the coil spring and facing a first direction and an opposing second surface extending along the length of the coil spring and facing a second direction opposite the first direction, wherein a portion of the first surface is configured to abut a portion of the second surface when the coil spring is in an unexpanded resting state, wherein the first surface has a concave shape and the second surface has a concave shape.

14. The spring hinge of claim 13, further comprising an interstitial coil spring having a helical structure with a central cavity, wherein the interstitial coil spring comprises a plurality of spirals, wherein each spiral of the plurality of spirals of the interstitial coil spring is disposed between adjacent spirals of the plurality of spirals of the coil spring.

15. The spring hinge of claim 14, wherein the interstitial coil spring deters sheering movement between the coil spring and the interstitial coil.

16. The spring hinge of claim 14, wherein the interstitial coil spring comprises a third surface extending along a length of the interstitial coil spring and facing the first direction and an opposing fourth surface extending along the length of the interstitial coil spring and facing the second direction.

17. The spring hinge of claim 16, wherein the third surface is convex and the fourth surface is convex.

18. The spring hinge of claim 17, wherein when the spring hinge is in an unexpanded state, the third surface is nested within a portion of the concave shape of the second surface and the fourth surface is nested within a portion of the concave shape of the first surface.

19. The spring hinge of claim 18, wherein when the spring hinge is in the unexpanded state, a portion of the third surface is in contact with the second surface and a portion of the fourth surface is in contact with the first surface.

20. An external fixation system, comprising:
a coil spring having a helical structure with a central cavity, wherein the coil spring comprises a plurality of spirals;
wherein the coil spring comprises a non-circular cross-sectional shape including a first surface extending along a length of the coil spring and facing a first direction and an opposing second surface extending along the length of the coil spring and facing a second direction opposite the first direction, the coil spring being configured such that the first surface contacts the second surface when the coil spring is in a resting state;
wherein the first surface and the second surface are shaped to permit adjacent spirals of the plurality of spirals to nest and configured to deter sheering movement between adjacent spirals of the plurality of spirals while permitting angular bending of the coil spring.

21. A method for treating an anatomical joint dysfunction comprising:
fixing a first and a second portion of a limb on opposite sides of an anatomical joint with a first and a second external fixator, such that the first and second external fixators are positioned on either side of the anatomical joint;
connecting the first and second external fixators with an orthopedic spring hinge, wherein the orthopedic spring hinge comprises:
a coil spring having a helical structure with a central cavity, wherein the coil spring comprises a plurality of spirals having a non-circular cross-sectional shape, the coil spring including a first end and a second end;
a first end cap coupled to the first end of the coil spring and including a first portion configured to mount the first end cap to the first external fixator; and
a second end cap coupled to the second end of the coil spring and including a second portion configured to mount the second end cap to the second external fixator;
the coil spring comprising a first surface extending along a length of the coil spring and facing a first direction and an opposing second surface extending along the length of the coil spring and facing a second direction opposite the first direction;
wherein the first surface and the second surface are shaped to permit adjacent spirals of the plurality of spirals to nest and deter sheering movement between adjacent spirals of the plurality of spirals while permitting angular bending of the coil spring, wherein the external fixators are adjusted to treat the anatomical joint dysfunction.

22. A method for treating an anatomical joint dysfunction comprising:
fixing a first and a second portion of a limb on opposite sides of an anatomical joint with a first and a second external fixator, such that the first and second external fixators are positioned on either side of the anatomical joint; and
connecting the first and second external fixators with an orthopedic spring hinge, wherein the orthopedic spring hinge comprises:

a coil spring having a helical structure with a central cavity extending along a central lengthwise axis, wherein the coil spring comprises a plurality of spirals having a non-circular cross-sectional shape in a plane in which the central lengthwise axis is disposed;

wherein the coil spring comprises a non-circular cross-sectional shape including a first surface extending along a length of the coil spring and facing a first direction and an opposing second surface extending along the length of the coil spring and facing a second direction opposite the first direction, the coil spring being configured such that the first surface contacts the second surface when the coil spring is in a resting state;

wherein the first surface and the second surface are configured to deter sheering movement between adjacent spirals of the plurality of spirals while permitting angular bending of the coil spring.

\* \* \* \* \*